(12) United States Patent
Drew

(10) Patent No.: US 9,357,949 B2
(45) Date of Patent: Jun. 7, 2016

(54) USER INTERFACE THAT DISPLAYS MEDICAL THERAPY AND POSTURE DATA

(75) Inventor: Touby A. Drew, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 1245 days.

(21) Appl. No.: 12/985,127

(22) Filed: Jan. 5, 2011

(65) Prior Publication Data

US 2011/0172564 A1    Jul. 14, 2011

Related U.S. Application Data

(60) Provisional application No. 61/293,541, filed on Jan. 8, 2010.

(51) Int. Cl.
*A61N 1/36* (2006.01)
*A61B 5/11* (2006.01)
(Continued)

(52) U.S. Cl.
CPC .............. *A61B 5/1116* (2013.01); *A61B 5/061* (2013.01); *A61B 5/4824* (2013.01);
(Continued)

(58) Field of Classification Search
CPC ........... A61N 1/36071; A61N 1/36128; A61N 1/36132; A61N 1/36135; A61N 1/36535; A61N 1/37235; A61N 1/37247; A61N 1/37211
USPC .............................. 607/30, 42, 46, 59, 60, 62
See application file for complete search history.

(56) References Cited

U.S. PATENT DOCUMENTS

| 4,297,685 A | 10/1981 | Brainard, II |
| 4,365,633 A | 12/1982 | Loughman |

(Continued)

FOREIGN PATENT DOCUMENTS

| DE | 19831109 | 1/2000 |
| DE | 10024103 | 11/2001 |

(Continued)

OTHER PUBLICATIONS

"Analysis of heart rate dynamics by methods derived from non-linear mathematics: Clinical applicability and prognostic significance," http://herkules.oulu.fi.isbn9514250133/html, 4 pp., 2004.

(Continued)

*Primary Examiner* — Allen Porter, Jr.
(74) *Attorney, Agent, or Firm* — Shumaker & Sieffert, P.A.

(57) ABSTRACT

The disclosure relates to a system that displays posture state information, physiological conditions of a patient on an avatar or other graphical representation of a human body, and therapy parameter information to facilitate the programming of therapy that is delivered to a patient. In some examples, the system may include an implantable medical device (IMD) that delivers therapy to a patient and incorporates a posture state module that detects a posture state engaged by the patient to determine the therapy delivered to the patient. An external programming device may communicate with the IMD, e.g., in real-time, to display the posture state of the patient as well as therapy parameters and physiological conditions associated with the posture state of the patient. The external programming device may receive adjustment input from the clinician to adjust one or more therapy parameters for therapy delivered to a patient in a specific posture state. In some examples, the external programming device may retrieve therapy information from the IMD to allow the clinician to review and play back previously stored therapy information on a temporal basis.

23 Claims, 19 Drawing Sheets

(51) Int. Cl.
*A61B 5/06* (2006.01)
*A61B 5/00* (2006.01)
*G06F 19/00* (2011.01)
*A61N 1/372* (2006.01)

(52) U.S. Cl.
CPC ....... *A61N 1/36071* (2013.01); *G06F 19/3406* (2013.01); *G06F 19/3481* (2013.01); *A61B 5/1118* (2013.01); *A61B 5/686* (2013.01); *A61B 2560/0219* (2013.01); *A61B 2562/0219* (2013.01); *A61N 1/37247* (2013.01)

(56) References Cited

U.S. PATENT DOCUMENTS

| | | | |
|---|---|---|---|
| 4,543,955 A | 10/1985 | Schroeppel | |
| 4,550,736 A | 11/1985 | Broughton et al. | |
| 4,566,456 A | 1/1986 | Koning et al. | |
| 4,771,780 A | 9/1988 | Sholder | |
| 4,776,345 A | 10/1988 | Cohen et al. | |
| 4,846,180 A | 7/1989 | Buffet | |
| 4,846,195 A | 7/1989 | Alt | |
| 5,031,618 A | 7/1991 | Mullett | |
| 5,040,534 A | 8/1991 | Mann et al. | |
| 5,040,536 A | 8/1991 | Riff | |
| 5,058,584 A | 10/1991 | Bourgeois | |
| 5,125,412 A | 6/1992 | Thornton | |
| 5,154,180 A | 10/1992 | Blanchet et al. | |
| 5,158,078 A | 10/1992 | Bennett et al. | |
| 5,167,229 A | 12/1992 | Peckham et al. | |
| 5,233,984 A | 8/1993 | Thompson | |
| 5,275,159 A | 1/1994 | Griebel | |
| 5,312,446 A | 5/1994 | Holschbach et al. | |
| 5,335,657 A | 8/1994 | Terry, Jr. et al. | |
| 5,337,758 A | 8/1994 | Moore et al. | |
| 5,342,409 A | 8/1994 | Mullett | |
| 5,354,317 A | 10/1994 | Alt | |
| 5,425,750 A | 6/1995 | Moberg | |
| 5,476,483 A | 12/1995 | Bornzin et al. | |
| 5,487,755 A | 1/1996 | Snell et al. | |
| 5,513,645 A | 5/1996 | Jacobson et al. | |
| 5,514,162 A | 5/1996 | Bornzin et al. | |
| 5,558,640 A | 9/1996 | Pfeiler et al. | |
| 5,562,707 A | 10/1996 | Prochazka et al. | |
| 5,593,431 A | 1/1997 | Sheldon | |
| 5,622,428 A | 4/1997 | Bonnet | |
| 5,628,317 A | 5/1997 | Starkebaum et al. | |
| 5,643,332 A | 7/1997 | Stein | |
| 5,645,053 A | 7/1997 | Remmers et al. | |
| 5,674,258 A | 10/1997 | Henschel et al. | |
| 5,711,316 A | 1/1998 | Elsberry et al. | |
| 5,720,770 A | 2/1998 | Nappholz et al. | |
| 5,732,696 A | 3/1998 | Rapoport et al. | |
| 5,741,310 A | 4/1998 | Wittkampf | |
| 5,782,884 A | 7/1998 | Stotts et al. | |
| 5,814,093 A | 9/1998 | Stein | |
| 5,832,932 A | 11/1998 | Elsberry et al. | |
| 5,833,709 A | 11/1998 | Rise et al. | |
| 5,836,989 A | 11/1998 | Shelton | |
| 5,851,193 A | 12/1998 | Arikka et al. | |
| 5,865,760 A | 2/1999 | Lidman et al. | |
| 5,885,471 A | 3/1999 | Ruben et al. | |
| 5,893,883 A | 4/1999 | Torgerson et al. | |
| 5,895,371 A | 4/1999 | Levitas et al. | |
| 5,904,708 A | 5/1999 | Goedeke | |
| 5,911,738 A | 6/1999 | Sikorski et al. | |
| 5,913,727 A | 6/1999 | Ahdoot | |
| 5,919,149 A | 7/1999 | Allum | |
| 5,938,690 A | 8/1999 | Law et al. | |
| 5,941,906 A | 8/1999 | Barreras, Sr. et al. | |
| 5,944,680 A | 8/1999 | Christopherson et al. | |
| 5,957,957 A | 9/1999 | Sheldon | |
| 5,984,368 A | 11/1999 | Cain | |
| 6,027,456 A | 2/2000 | Feler et al. | |
| 6,038,475 A | 3/2000 | Sikorski et al. | |
| 6,044,297 A | 3/2000 | Sheldon et al. | |
| 6,045,513 A | 4/2000 | Stone et al. | |
| 6,059,576 A | 5/2000 | Brann | |
| 6,095,991 A | 8/2000 | Krausman et al. | |
| 6,099,479 A | 8/2000 | Christopherson et al. | |
| 6,102,874 A | 8/2000 | Stone et al. | |
| 6,120,467 A | 9/2000 | Schallhorn | |
| 6,128,534 A | 10/2000 | Park et al. | |
| 6,134,459 A | 10/2000 | Roberts et al. | |
| 6,157,857 A | 12/2000 | Dimpfel | |
| 6,165,143 A | 12/2000 | Van Lummel | |
| 6,216,537 B1 | 4/2001 | Henschel et al. | |
| 6,259,948 B1 | 7/2001 | Florio et al. | |
| 6,280,409 B1 | 8/2001 | Stone et al. | |
| 6,296,606 B1 | 10/2001 | Goldberg et al. | |
| 6,308,098 B1 | 10/2001 | Meyer | |
| 6,308,099 B1 | 10/2001 | Fox et al. | |
| 6,315,740 B1 | 11/2001 | Singh | |
| 6,327,501 B1 | 12/2001 | Levine et al. | |
| 6,341,236 B1 | 1/2002 | Osorio et al. | |
| 6,351,672 B1 | 2/2002 | Park et al. | |
| 6,368,284 B1 | 4/2002 | Bardy | |
| 6,381,496 B1 | 4/2002 | Meadows et al. | |
| 6,393,325 B1 | 5/2002 | Mann et al. | |
| 6,438,408 B1 | 8/2002 | Mulligan et al. | |
| 6,440,090 B1 | 8/2002 | Schallhorn | |
| 6,449,508 B1 | 9/2002 | Sheldon et al. | |
| 6,459,934 B1 | 10/2002 | Kadhiresan | |
| 6,466,821 B1 | 10/2002 | Pianca et al. | |
| 6,468,234 B1 | 10/2002 | Van der Loos et al. | |
| 6,507,757 B1 | 1/2003 | Swain et al. | |
| 6,514,218 B2 | 2/2003 | Yamamoto | |
| 6,516,749 B1 | 2/2003 | Salasidis | |
| 6,539,249 B1 | 3/2003 | Kadhiresan et al. | |
| 6,547,755 B1 | 4/2003 | Lippe et al. | |
| 6,572,557 B2 | 6/2003 | Tchou et al. | |
| 6,574,507 B1 | 6/2003 | Bonnet | |
| 6,605,038 B1 | 8/2003 | Teller et al. | |
| 6,609,031 B1 | 8/2003 | Law et al. | |
| 6,611,783 B2 | 8/2003 | Kelly, Jr. et al. | |
| 6,620,151 B2 | 9/2003 | Blischak et al. | |
| 6,625,493 B2 | 9/2003 | Kroll et al. | |
| 6,635,048 B1 | 10/2003 | Ullestad et al. | |
| 6,641,542 B2 | 11/2003 | Cho et al. | |
| 6,658,292 B2 | 12/2003 | Kroll et al. | |
| 6,659,968 B1 | 12/2003 | McClure | |
| 6,662,047 B2 | 12/2003 | Sorensen | |
| 6,665,558 B2 | 12/2003 | Kalgren et al. | |
| 6,668,188 B2 | 12/2003 | Sun et al. | |
| 6,687,538 B1 | 2/2004 | Hrdlicka et al. | |
| 6,731,984 B2 | 5/2004 | Cho et al. | |
| 6,740,075 B2 | 5/2004 | Lebel et al. | |
| 6,748,276 B1 | 6/2004 | Daignault, Jr. et al. | |
| 6,752,766 B2 | 6/2004 | Kowallik et al. | |
| 6,773,404 B2 | 8/2004 | Poezevera et al. | |
| 6,782,315 B2 | 8/2004 | Lu et al. | |
| 6,817,979 B2 | 11/2004 | Nihtilä | |
| 6,820,025 B2 | 11/2004 | Bachmann et al. | |
| 6,829,507 B1 | 12/2004 | Lidman et al. | |
| 6,832,113 B2 | 12/2004 | Belalcazar | |
| 6,834,436 B2 | 12/2004 | Townsend | |
| 6,853,863 B2 | 2/2005 | Carter et al. | |
| 6,878,121 B2 | 4/2005 | Krausman et al. | |
| 6,884,596 B2 | 4/2005 | Civelli et al. | |
| 6,890,306 B2 | 5/2005 | Poezevera | |
| 6,895,341 B2 | 5/2005 | Barrey et al. | |
| 6,922,587 B2 | 7/2005 | Weinberg | |
| 6,923,784 B2 | 8/2005 | Stein | |
| 6,928,324 B2 | 8/2005 | Park et al. | |
| 6,937,899 B2 | 8/2005 | Sheldon et al. | |
| 6,937,900 B1 | 8/2005 | Pianca et al. | |
| 6,945,934 B2 | 9/2005 | Bardy | |
| 6,964,641 B2 | 11/2005 | Cho et al. | |
| 6,975,904 B1 | 12/2005 | Sloman | |
| 6,997,882 B1 | 2/2006 | Parker et al. | |
| 6,999,817 B2 | 2/2006 | Park et al. | |
| 7,016,730 B2 | 3/2006 | Ternes | |
| 7,031,772 B2 | 4/2006 | Condie | |
| 7,043,305 B2 | 5/2006 | KenKnight et al. | |

(56) References Cited

U.S. PATENT DOCUMENTS

| | | |
|---|---|---|
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al. |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann et al. |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 8,538,527 B2 * | 9/2013 | Goetz ............... A61N 1/08 607/117 |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0107722 A1 * | 5/2005 | Ozaki et al. .................. 600/587 |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0287686 A1 | 12/2006 | Cullen et al. |
| 2007/0015976 A1 | 1/2007 | Miesel et al. |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1 | 5/2007 | Wang et al. |

(56) References Cited

U.S. PATENT DOCUMENTS

| | | |
|---|---|---|
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1 | 5/2008 | Zhang et al. |
| 2008/0154340 A1* | 6/2008 | Goetz ............... A61N 1/37247 607/59 |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |
| 2010/0280440 A1* | 11/2010 | Skelton ............... A61N 1/37247 604/66 |
| 2011/0172738 A1* | 7/2011 | Davis .................. A61B 5/0031 607/59 |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| EP | 2110067 A1 | 10/2009 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2007127455 A2 | 11/2007 |
| WO | 2008/026970 | 3/2008 |

OTHER PUBLICATIONS

"Design Competition: Runners-Up for the Best Three Designs," EPN, vol. 26, No. 1, 1 pg., 2002.

IBM and Citizen Watch develop Linux-Based "WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org.wiki/Watch, 2006.

(56) References Cited

OTHER PUBLICATIONS

Aminian et al., "Physical Activity Monitoring Based on Accelerometry: Validation and Comparison with Video Observation," Medical & Biological Engineering and Computing, vol. 37, No. 2, pp. 304-308,1999.
Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.
Ang et al., "Physical model of a MEMS accelerometer for low-g motion tracking applications," 2004 IEEE International Conference on Robotics and Automation, vol. 2, pp. 1345-1351, 2004.
Buchser et al., "Improved Physical Activity in Patients Treated for Chronic Pain by Spinal Cord Stimulation," Neuromodulation, vol. 8, Issue 1, pp. 40-48, Mar. 2005.
Crago et al., "An Elbow Extension Neuroprosthesis for Individuals with Tetraplegia," IEEE Transactions on Rehabilitation Engineering, vol. 6, No. 1, pp. 1-6, Mar. 1998.
Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.
Dinner, "Effect of Sleep on Epilepsy," Journal of Clinical Neurophysiology, American Clinical Neurophysiology Society, 19(6), pp. 504-513, 2002.
Foerster et al., "Motion Pattern and Posture: Correctly Assessed by Calibrated Accelerometers," Forschungsgrupe Psychophysiologie, Universität Freiburg, Germany, Mar. 2000, 28 pp.
Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.
Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.
Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.
Goodrich et al., "The Prediction of Pain Using Measures of Sleep Quality," Pain Digest, 8:23-25, 1998.
Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006 5 pp. http://eis.comp.lancs.ac.uk/fileadmin/relate/publication/2006-WearableSensors.pdf.
Hendelman et al., "Validity of Accelerometry for the Assessment of Moderate Intensity Physical Activity in the Field," Medicine & Science in Sports & Exercise, pp. S442-S449, 2000.
Husak, "Model of Tilt Sensor Systems, "ICECS 2002, 9th IEEE International Conference on Electronics, Circuits and Systems, vol. 1, pp. 227-230, 2002.
Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.
Kassam, "2005 EDP Topic "MK4": Tremor Data-Logger for Parkinson's Disease Patients," http://www.ee.ryerson.ca/~courses/edp2005/MK4.html, 3 pp., 2005.
Kerr et al., "Analysis of the sit-stand-sit movement cycle in normal subjects," Clinical Biomechanics, vol. 12, No. 4, pp. 236-245, 1977.
Kiani et al., "Computerized Analysis of Daily Life Motor Activity for Ambulatory Monitoring," Technology and Health Care 5, pp. 307-318, 1997.
Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.
Leiper et al., "Sensory Feedback for Head Control in Cerebral Palsy," Physical Therapy, vol. 61, No. 4, pp. 512-518, Apr. 1981.
Lorussi, "Wearable, Redundant Fabric-Based Sensor Arrays for Reconstruction of Body Segment Posture," IEEE Sensors Journal, vol. 4, No. 6, pp. 808-817, Dec. 2004.
Mathie et al., "A Pilot Study of Long-Term Monitoring of Human Movements in the Home Using Accelerometer," Journal of Telemedicine and Telecare10:144-151, Jun. 2007.
Mathie et al., "Determining Activity Using a Triaxial Accelerometer," Proceedings of the Second Joint EMBS/BMES Conference, Houston, TX, pp. 2481-2482, Oct. 23-26, 2002.
Mattmann et al., "Recognizing Upper Body Postures Using Textile Strain Sensors," Proceedings Eleventh IEEE International Symposium on Wearable Computers, ISWC, pp. 29-36, 2007.
Mendez et al., "Interactions Between Sleep and Epilepsy," Journal of Clinical Neurophysiology, American Clinical Neurophysiology Society, 18(2), pp. 106-127, 2001.
Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.
Slyper et al., "Action Capture with Accelerometers," Eurographics/ACM SIGGRAPH Symposium on Computer Animation, Carnegie Mellon University, 7 pp. 2008.
Smith et al., "How do sleep disturbance and chronic pain inter-relate? Insights from the longitudinal and cognitive-behavioral clinical trials literature," Sleep Medicine Reviews, YSMRV 286, pp. 1-14, 2003.
Smith et al., "Presleep cognitions in Patients with Insomnia Secondary to Chronic Pain," Journal of Behavioral Medicine, vol. 24, No. 1, pp. 93-114, 2001.
Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.
Trolier-Mckinstry et al., "Thin Film Piezoelectrics for MEMS," Journal of Electroceramics, v. 12, No. 1-2, pp. 7-17, Jan./Mar. 2004.
Tuck, "Implementing Auto-Zero Calibration Technique for Accelerometers," Freescale Semiconductor Application Note AN3447, 5 pp., Mar. 2007.
Tuisku, "Motor Activity Measured by Actometry in Neuropsychiatric Disorders," Department of Psychiatry, University of Helsinki, Helsinki, Finland, 115 pp., 2002.
Vega-Gonzalez, "Upper Limb Activity Monitoring," Arch Phys Med Rehabil, vol. 86, pp. 541-548, Mar. 2005.
Velten et al., "A New Three-Axis Accelerometer," Sensor '99—9th Int'l Traide Fair and Conference for Sensors/Transducers & Systems, Nürnberg, Germany, May 18-20, 1999, Sensor '99 Proceedings II, A 5.2, pp. 47-52, 1999.
U.S. Appl. No. 12/815,834, filed Jun. 15, 2010, Gerber et al.
U.S. Appl No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.

(56) References Cited

OTHER PUBLICATIONS

U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.
U.S. Appl. No. 12/895,919, filed Jan. 6, 2011, Davis et al.
U.S. Appl. No. 61/293,393, filed Jan. 8, 2010, Davis et al.
U.S. Appl. No. 61/330,063, filed Apr. 30, 2010, Davis et al.

International Search Report and Written Opinion dated May 20, 2011 for corresponding PCT Application No. PCT/US2011/020568, (9 pgs.).
Office Action from U.S. Appl. No. 12/433,103, dated Sep. 19, 2014, 14 pp.
Notice of Allowance from U.S. Appl. No. 12/433,103, dated Jan. 14, 2015, 11 pp.
Response to Office Action dated Sep. 18, 2014, from U.S. Appl. No. 12/433,103, dated Dec. 18, 2014, 14 pp.
Office Action from U.S. Appl. No. 14/699,847, dated Jun. 12, 2015, 11 pp.
Notice of Allowance from U.S. Appl. No. 14/699,847, mailed Oct. 15, 2015, 9 pp.
Hinckley et al., "Sensing Techniques for Mobile Interaction," ACM UIST 2000 Symposium on User Interface Software & Technology, CHI Letters vol. 2 No. 2, Nov. 2000, pp. 91-100, 10 pp.
Kitchin et al., "Compensating for the 0 g Offset Drift of the ADXL50 Accelerometer," Analog Devices Application Note AN-380, May 1994, 2 pp.

\* cited by examiner

USER INTERFACE THAT DISPLAYS MEDICAL THERAPY AND POSTURE DATA This application claims the benefit of U.S. Provisional Application No. 61/293,541 by Drew, entitled, "USER INTERFACE THAT DISPLAYS MEDICAL THERAPY AND POSTURE DATA" and filed on Jan. 8, 2010, the entire content of which is incorporated herein by reference.

TECHNICAL FIELD

The disclosure relates to medical devices and, more particularly, to user interfaces for use with medical devices.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

Initially, a clinician uses an external device, e.g., a clinician programmer, to provide a set, or multiple sets, of stimulation parameters that instruct the medical device how to deliver the therapy to the patient. This "programming" task usually occurs once the medical device is implanted in the patient and ready for operation. In some situations, the initial stimulation parameters are merely the best estimate of the clinician as to what type of therapy will alleviate the patient of their physiological symptoms or conditions. The patient may thus need to visit the clinician periodically to subsequently adjust the stimulation parameters for more effective treatment.

In some cases, the patient may be allowed to activate and/or modify the therapy delivered by the medical device. For example, a patient may be provided with a patient programming device. The patient programming device communicates with a medical device to allow the patient to activate therapy and/or adjust therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure relates to medical therapy devices and systems that present therapy information to a user, such as, e.g., a clinician, via a user interface display of an external device. The therapy information may be presented to the user for use in conjunction with an implantable medical device (IMD), or other medical device, configured to detect the posture state occupied by the patient and deliver therapy to the patient based on the detected posture state. In some examples, the therapy information presented to a user by the user interface of the external programming device may aid in the programming of various parameters for therapy delivered to a patient via the medical device.

In one example, the disclosure relates to a method including displaying a posture state field representative of a posture state of a patient; displaying at least one graphical representation representative of at least a portion of a body of the patient; overlaying a physiological condition indicator over at least a portion of the graphical representation, wherein the physiological condition indicator is indicative of a physiological condition of the patient associated with the posture state by the patient; and displaying at least one of a plurality of therapy parameters that define therapy delivered to the patient.

In another example, the disclosure relates to a system including an external device including a user interface, wherein the user interface is configured to display a posture state field representative of a posture state of a patient, display at least one graphical representation representative of at least a portion of a body of the patient, overlay a physiological condition indicator over at least a portion of the graphical representation, and display at least one of a plurality of therapy parameters that define therapy delivered to the patient, wherein the physiological condition indicator is indicative of a physiological condition of the patient associated with the posture state by the patient.

In another example, the disclosure is directed to a system comprising means for displaying a posture state field representative of a posture state of a patient; means for displaying at least one graphical representation representative of at least a portion of a body of the patient; means for overlaying a physiological condition indicator over at least a portion of the graphical representation, wherein the physiological condition indicator is indicative of a physiological condition of the patient associated with the posture state by the patient; and means for displaying at least one of a plurality of therapy parameters that define therapy delivered to the patient.

In an additional example, the disclosure relates to a non-transitory computer-readable storage medium including instructions that causes a processor to control a user interface of an external device to display a posture state field representative of a posture state of a patient; display at least one graphical representation representative of at least a portion of a body of the patient; overlay a physiological condition indicator over at least a portion of the graphical representation, wherein the physiological condition indicator is indicative of a physiological condition of the patient associated with the posture state by the patient; and display at least one of a plurality of therapy parameters that define therapy delivered to the patient.

In another example, the disclosure is directed to a non-transitory computer-readable storage medium comprising instructions. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein. The computer-readable storage medium may be an article of manufacture, and may be non-transitory.

The details of one or more aspects of the disclosure are set forth in the accompanying drawings and the description below. Other features, objects, and advantages will be apparent from the description and drawings, and from the claims.

DETAILED DESCRIPTION

Figure 1A:
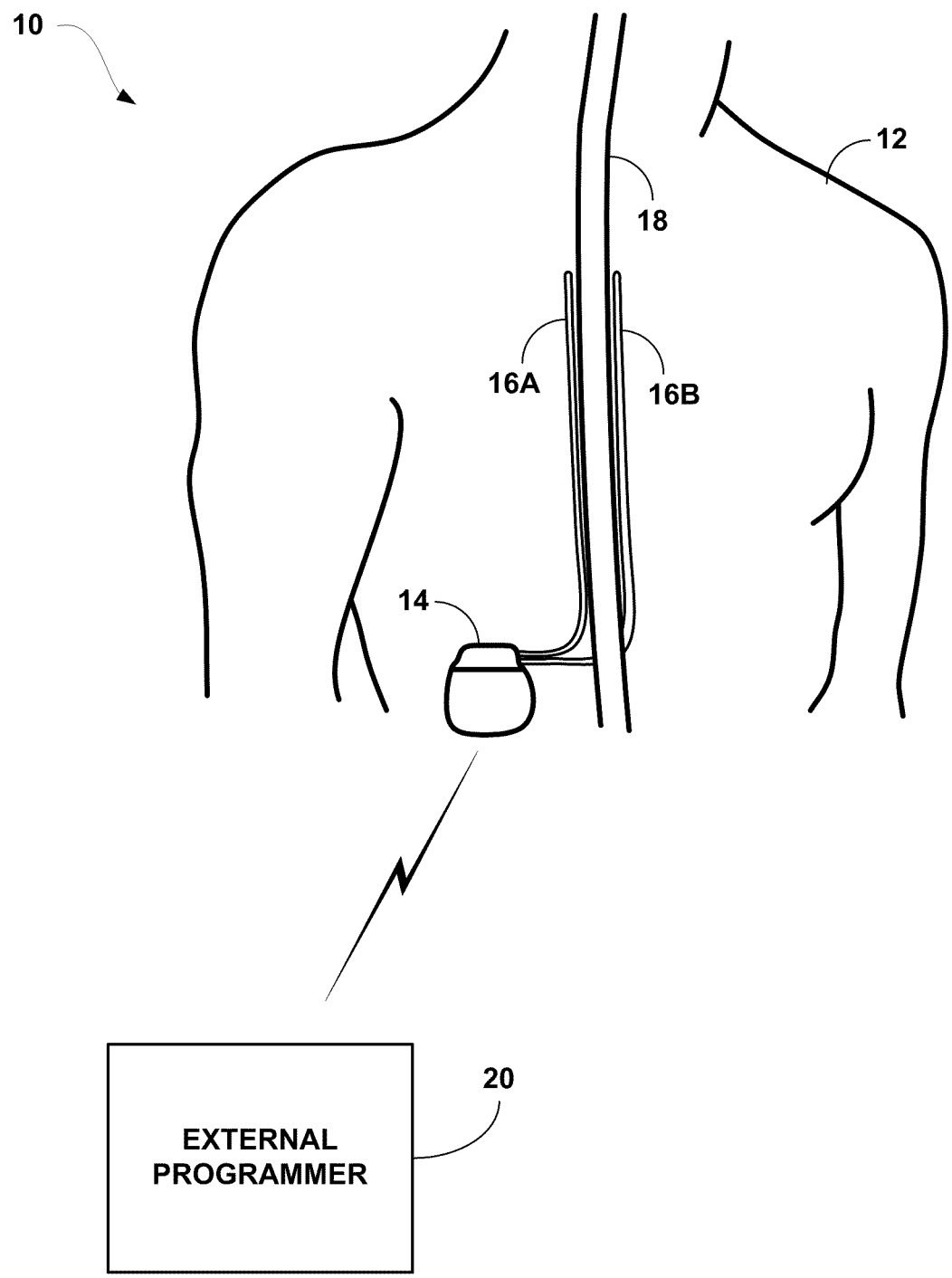
FIG. 1A is a conceptual diagram illustrating an implantable stimulation system including two implantable stimulation leads.

As described above, in some examples, an IMD may be configured to deliver therapy based upon a detected posture state of the patient. For example, in the case of an IMD that delivers electrical stimulation therapy, the IMD may utilize information regarding the detected posture state of patient to determine what stimulation parameters are used for therapy to target certain symptoms that may change with different anatomical positions of the patient. These therapeutic changes due to posture states can be important to therapy programming, and it may be useful for the clinician and patient to visualize how patient symptoms and therapy delivered to the patient changes with the posture state of a patient. In some examples, this disclosure describes a system that presents this posture state information in real-time or historically, along with other therapy information, in order to facilitate programming efficacious therapy.

Changes in the posture state of a patient receiving therapy from an IMD may cause changes in therapeutic efficacy. In some examples, such changes may be due to changes in distances between electrodes or other therapy delivery elements, e.g., due to temporary migration of leads or catheters with respect to patient physiology caused by forces or stresses associated with different postures of the patient, or from changes in compression of patient tissue in different posture states. To maintain the delivery of effective therapy, it may be desirable to adjust therapy parameters based on different postures and/or activities engaged by the patient. In the case of electrical stimulation therapy delivered in pulses, therapy parameters may include amplitude (voltage or current), pulse rate, pulse width, electrode polarity, and electrode combination. Such therapy parameter values may be adjusted individually or by selecting different programs or groups of programs defining different sets of therapy parameters.

Without posture based therapy, the patient may need to continually manage therapy by manually adjusting the values of certain therapy parameters or selecting different therapy programs to achieve more efficacious therapy throughout many different posture states. However, programming different therapy parameter values for each of a plurality of patient posture states may be an additional burden on the clinician or patient. Therefore, a user interface that incorporates patient posture state information along with other related data such as patient physiological conditions (e.g., physiological symptoms) and proposed or programmed therapy parameters may be useful for initial therapy programming and subsequent follow-up programming of therapy delivered according to the posture state of a patient.

As described above, the disclosure relates to medical therapy devices and systems that present therapy information to a user, such as, e.g., a clinician, via a user interface display of an external device. The therapy information may be presented to the user for use in conjunction with an IMD, or other medical device, configured to detect the posture state occupied by the patient and deliver therapy to the patient based on the detected posture state. In some examples, the therapy information presented to a user by the user interface of the external programming device may aid in the programming of various parameters of therapy delivered to a patient via the medical device.

Therapy information associated with the therapy delivered to the patient via the IMD may be organized and presented by the user interface display on a posture state specific basis. In some examples, the therapy information presented by the user interface display may include a posture state field that indicates a posture state of a patient to a user. For example, the posture state field presented by the display may include one or more of a graphical or textual indication of a patient posture state.

In addition to the posture state field, the system may utilize an avatar or other graphical indicator representative of at least a portion of the body of the patient to display physiological conditions of the patient that are associated with the specific posture state indicated by the posture state field in relation to specific physiological areas of the body. Physiological condition information presented by the user interface for a posture state may include pain, paresthesia or other physiological sensations experienced by the patient that may be relevant to the patient condition or therapy delivered by an IMD to the patient to treat the condition.

Physiological condition information may be unique for each posture state of the patient that may be detected by the IMD. Such physiological condition information may be overlaid on the avatar or other graphical representation of all or a portion of the human body to represent the physiological location at which the patient experienced or is experiencing the physiological conditions along with the posture state of the patient corresponding to the physiological conditions. By displaying such information, a dermatome, pain map, paresthesia map, and/or the like may be presented to a user in conjunction with an indication of the specific posture state for which the physiological conditions have been associated to allow the user to visualize the physiological conditions of the patient for a particular patient posture state in combination with particular therapy settings, which may be represented by therapy parameter information.

The user interface display may also present therapy parameter information in addition to the display of postures state field and physiological condition information. In some examples, the therapy parameter information may be associated with the posture state indicated by the posture state field, e.g., therapy parameter information for therapy that has been delivered in the past or that is programmed for delivery in the future to the patient when the indicated posture state is detected by the IMD.

In some examples, the therapy parameter information may be presented in the form of textual parameter values for one or more therapy parameters. For example, in the case of electrical stimulation therapy including stimulation pulses, the user interface may display text indicating values for one or more of pulse rate, pulse amplitude (voltage or current), pulse frequency, electrode polarity and electrode configuration. Additionally or alternatively, the therapy parameter information may include an indication of the therapy programs, therapy groups, and/or program slots to a user. The therapy parameter information displayed by the user interface may correspond to the therapy parameters for therapy that has been previously delivered to a patient and/or those parameters currently programmed for therapy delivered to the patient in the posture state indicated by the concurrently presented posture state field. In some examples, therapy parameter information may include one or more parameters defined for the adjustment between therapy parameter values, e.g., that may accompany a transition in postures states. For example, a ramp or transition profile for pulse amplitude defined for a posture state transition may be displayed to a user. As will be described is further detail below, in some examples, a user may be allowed to input adjustments to one or more therapy parameters via the user interface, which may then be communicated to the IMD for delivery of therapy for the indicated patient posture state.

Additionally or alternatively, therapy parameter information may be presented graphically in the form of therapy stimulation fields representative of the stimulation field generated by stimulation therapy. In the case of a therapy including drug delivery to a patient, e.g., via a drug pump device, the field of influence of the drug being delivered, which may be influenced by factors like drug density, implant location, posture, CSF flow or the like. The therapy stimulation field may be generated based on therapy parameters values defined for a particular therapy. In some examples, the therapy fields may displayed in conjunction with a physiological image to help a user visualize the stimulation field in the patient. For example, an atlas or other medical image (e.g., a post-operative medical image) representing the location of one or more stimulation leads (or catheter in the case of drug infusion therapy) within a patient may be displayed by the user interface in conjunction with stimulation therapy fields to assist a clinician in visualizing the stimulation field generated by simulation delivered to the target tissue site in the patient. In some examples, images indicating the location of device components within a patient may be presented without stimulation fields. In this manner, a user may visualize the location of device components (e.g., leads, electrodes, catheters) within patient and/or stimulation fields corresponding to selected therapy parameters, in conjunction with the physiological conditions and postures state field concurrently presented by the user interface display.

The postures state field information, physiological condition information, therapy parameter information, or other therapy information may be displayed by the user interface of the external device simultaneously to provide an integrated representation of patient conditions and therapy parameters associated with a particular posture state of a patient. Therapy information presented by the user interface may incorporate graphical icons to reduce the volume of information into graphical icons, but detailed information such as individual stimulation parameters may be obtained with minimal additional interaction with the user interface. Therapy information displayed to a user via an external therapy device may include historical therapy information previously stored over one or more different time periods.

At least a portion of the therapy information displayed on the user interface may be communicated from the IMD to an external device including the user interface display for presentation to a user. In some examples, the IMD may be configured to communicate therapy information to the external programming device in real-time by streaming data in real-time to the external user interface device. In such cases, the posture state field displayed by the user interface may indicate the current posture state of the patient detected by the IMD and communicated to the user interface device in real-time.

The therapy parameters and physiological conditions associated with the posture state of the patient detected by an IMD may be updated in real-time along with the posture state field on the user interface display. For example, when the IMD detects a change in patient posture state from a first posture state to a second posture state (e.g., from a lying to standing posture state), the user interface may update the posture field presented to a user to represent the second posture state and also update the display to represent physiological condition and therapy parameter information associated with the second posture state from that associated with the first posture state. In this manner, the user interface display may present therapy information to a clinician, e.g., during a programming session, that corresponds to the posture state currently occupied by a patient. To change the therapy information displayed by the user interface, a clinician may instruct the patient to transition to another posture state. The IMD may detect the change in the posture state of the patient, at which time the user interface may be updated to display therapy information associated with the new posture state of the patient from that of the therapy information associated with the previous posture state of the patient. In other examples, a clinician select a particular posture state of a patient, e.g., from a drop down menu, and the user interface may then update the display to reflect the selected postures state of the patient indicated by the posture state field, as well as display the physiological condition and therapy parameter information associated with the selected posture state.

Additionally or alternatively, the therapy information presented to a user via the user interface display may reflect historical therapy information. For example, the external device may retrieve therapy information from the IMD stored previously during patient therapy and then displayed to a user via the user interface display. As described above, therapy information may include, but is not limited to, patient physiological conditions, therapy parameters, patient posture states, patient adjustments to therapy parameters, and the like. In some examples, this historical therapy information may be reviewed by the clinician on a temporal basis to allow the clinician to play back and review the progression or sequences of therapy delivered to the patient. For example, during a programming session, a clinician may review therapy information for a patient from the time period subsequent the last programming session. In some cases, the clinician may select a particular posture state of the patient to review. In such cases, the user interface display may present a posture state field to the user along with physiological condition information and therapy parameter information associated with the posture state during the previous time period. In other examples, a user may selected a particular time or range of times to review the therapy parameter information and physiological condition information of the patient as well as the posture state(s) occupied by the patient during the selected time period.

The external device including the user interface display may communicate directly or indirectly with the implantable medical device (IMD) that delivers stimulation therapy to the patient. As described above, the IMD may stream data in real-time to the external device including the user interface display for a real-time representation of therapy parameters. In the case of historical review of therapy information, the user interface may provide playback of historical therapy information that has been stored in the IMD or other device over the course of patient therapy and then transmitted to the external user interface device, e.g., via wireless telemetry. In some examples, the historical therapy information may be organized by time and/or posture state, and the user interface may allow the therapy information to be viewed collectively by a user on a temporal basis. In some examples, a clinician may, in essence, "play back" the therapy, as represented by the displayed therapy information, as the therapy has progressed, forward or reverse through time, select a particular time, pause the information at an identified time, or filter therapy information according to posture state, stimulation parameters, patient conditions, or any other data. The user interface may provide this playback feature in conjunction with the real-time data or separately on the external device or other networked computing device. In other examples, the user interface may merely provide for real-time or playback review of therapy information, such as physiological condition information, therapy parameter information, and/or posture state information, without allowing the user to change stimulation parameters or perform other programming functions.

In addition to displaying therapy information to a user, the external user interface device may be configured to receive input from a user regarding the therapy information. For example, during a programming session, a clinician may be able to input adjustments therapy parameters displayed on the user interface display, e.g., for therapy defined for the posture state indicated concurrently by the posture field. In this manner, the user interface may receive adjustment input from the clinician to adjust one or more stimulation parameters to achieve more efficacious stimulation therapy.

Similarly, the user interface of the external device may also receive input regarding physiological conditions. For example, a patient may provide input regarding pain and/or paresthesia experienced when occupying a posture state, and the therapy information displayed by the user interface may be updated based on the patient feedback. The patient input may be used to initially populate physiological condition information for the display, e.g., during an initial programming session, or the patient input may be received after initial patient conditions have been established for particular postures states to update the physiological patient conditions as such physiological conditions may change over time.

In one example in which the user interface display presents therapy information in real-time, a patient may physically change posture states to cycle through the various postures states to change the posture state and therapy information displayed on the user interface as well as program one or more of therapy parameter information and physiological condition information for respective postures states. For example, when occupying a first posture state, the patient may input physiological condition information experienced for the first posture state. The external device may then associate the condition information with the first posture state. The patient may then transition to a second posture state and provide physiological conditions information for the second posture state that is occupied by the patient, which is then associated by the external device with the second posture state. In a similar fashion, one or more adjustment to therapy parameters may be inputted by a user when the patient actually occupies the posture state, which is indicated by the posture state field presented on the user interface display. In this manner, the input provided by a user is associated with the particular posture state intended by the user instead of requiring a user to select a particular posture state from a list of posture states that is estimated by the user to be the posture state intended to be associated with the inputted therapy information. Throughout such a process, the user interface may be continuously updated to display the detected posture state of the patient in conjunction with therapy information associated with the detected posture state.

FIG. 1A is a schematic diagram illustrating an implantable stimulation system 10 including a pair of implantable electrode arrays in the form of stimulation leads 16A and 16B. Although the techniques described in this disclosure may be generally applicable to a variety of medical devices including external and implantable medical devices (IMDs), application of such techniques to IMDs and, more particularly, implantable electrical stimulators such as neurostimulators will be described for purposes of illustration. In some examples, the disclosure will refer to an implantable spinal cord stimulation (SCS) system for purposes of illustration, but without limitation as to other types of medical devices.

As shown in FIG. 1A, system 10 includes an IMD 14 and external programmer 20 shown in conjunction with a patient 12. In the example of FIG. 1A, IMD 14 is an implantable electrical stimulator configured for spinal cord stimulation (SCS), e.g., for relief of chronic pain or other symptoms. Again, although FIG. 1A shows an implantable medical device, other embodiments may include an external stimulator, e.g., with percutaneously implanted leads. Stimulation energy is delivered from IMD 14 to spinal cord 18 of patient 12 via one or more electrodes of implantable leads 16A and 16B (collectively "leads 16"). In some applications, such as spinal cord stimulation (SCS) to treat chronic pain, the adjacent implantable leads 16 may have longitudinal axes that are substantially parallel to one another.

Although FIG. 1A is directed to SCS therapy, system 10 may alternatively be directed to any other condition that may benefit from stimulation therapy. For example, system 10 may be used to treat tremor, Parkinson's disease, anxiety, depression, epilepsy, urinary or fecal incontinence, sexual dysfunction, obesity, or gastroparesis. In this manner, system 10 may be configured to provide therapy taking the form of deep brain stimulation (DBS), peripheral nerve stimulation, pelvic floor stimulation, gastric stimulation, or any other stimulation therapy. Patient 12 is ordinarily a human patient.

Each of leads 16 may include one or more electrodes (not shown in FIG. 1A), and the parameters for a program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described in this disclosure for purposes of illustration. However, stimulation may be delivered in other forms such as continuous waveforms. Programs that control delivery of other therapies by IMD 14 may include other parameters, e.g., such as dosage amount, rate, or the like for drug delivery.

In the example of FIG. 1A, leads 16 carry one or more electrodes that are placed adjacent to the target tissue of the spinal cord. One or more electrodes may be disposed at a distal tip of a lead 16 and/or at other positions at intermediate points along the lead. Leads 16 may be implanted and coupled to IMD 14. Alternatively, as mentioned above, IMD 14 may be an external stimulator, in which case leads 16 may be implanted and coupled to an external stimulator, e.g., through a percutaneous port. As an external stimulator, IMD 14 may be a trial or screening stimulator that used on a temporary basis to evaluate potential efficacy to aid in consideration of chronic implantation for a patient. Additionally or alternatively, IMD 14 may be an external stimulator used chronically. In additional embodiments, IMD 14 may be a leadless stimulator with one or more arrays of electrodes arranged on a housing of the stimulator rather than leads that extend from the housing.

The stimulation may be delivered via selected combinations of electrodes carried by one or both of leads 16. The target tissue may be any tissue affected by electrical stimulation energy, such as electrical stimulation pulses or waveforms. Such tissue includes nerves, smooth muscle, and skeletal muscle. In the example illustrated by FIG. 1A, the target tissue is spinal cord 18. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some embodiments, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to the spinal cord 18 to reduce the amount of pain perceived by patient 12. As described above, IMD 14 may be used with a variety of different pain therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In some examples, IMD 14 may deliver stimulation therapy according to one or more programs. A program defines one or more stimulation parameters that define an aspect of the therapy delivered by IMD 14 according to that program. For example, a program that controls delivery of stimulation by IMD 14 in the form of pulses may define one or more therapy parameters such as a voltage or current pulse amplitude, a pulse width, a pulse rate, for stimulation pulses delivered by IMD 14 according to that program. Moreover, therapy may be delivered according to multiple programs, wherein multiple programs are contained within each of a multiple of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdominal pain. In this manner, IMD 14 may treat different symptoms substantially simultaneously.

In some examples, separate programs may be selected for a set of program slots. Each slot may include one or more programs that form therapy options for the slot, and each slot may target a different symptom or area of pain. One program may be selected from each slot, where the selection of a program in one slot is independent of the programs selected in other slots. In other words, therapy is defined by multiple slots, and each slot is defined by selection of one of a plurality of programs designated for the slot. In applying stimulation therapy, programs for different slots may be delivered on an interleaved or rotating basis. In some examples example, the programs in the slots may be delivered in fast succession such that a patient experiences near-constant paresthesia from the combined effect of each of the programs simultaneously. One or more examples of slot-based therapy programming may be described in co-pending U.S. Provisional Application No. 61/293,393, to Davis, et al., titled "PROGRAMMING THERAPY DELIVERED BY IMPLANTABLE MEDICAL DEVICE," and filed Jan. 8, 2010.

During use of IMD 14 to treat patient 12, movement of patient 12 among different posture states may affect the ability of IMD 14 to deliver consistent efficacious therapy. For example, leads 16 may migrate toward IMD 14 when patient 12 bends over, resulting in displacement of electrodes and possible disruption in delivery of effective therapy. For example, stimulation energy transferred to target tissue may be reduced due to electrode migration, causing reduced efficacy in terms of relief of symptoms such as pain. As another example, leads 16 may be compressed towards spinal cord 18 when patient 12 lies down. Such compression may cause an increase in the amount of stimulation energy transferred to target tissue. In this case, the amplitude of stimulation therapy may need to be decreased to avoid causing patient 12 additional pain or unusual sensations, which may be considered undesirable side effects that undermine overall efficacy.

Also, posture state changes may present changes in symptoms or symptom levels, e.g., pain level. In some examples, to avoid interruptions in effective therapy, IMD 14 may include a posture state module that detects the patient posture state. The IMD automatically adjusts stimulation according to the detected posture state of patient 12, thereby providing posture state responsive therapy. For example, the posture state module may include one or more accelerometers that detect when patient 12 occupies a posture state in which it is appropriate to decrease the stimulation amplitude, e.g., when patient 12 lies down. The IMD may automatically reduce stimulation amplitude so that patient 12 does not manually have to do so. Example posture states may include "Upright," "Upright and Active," "Lying Front," "Lying Left," "Lying Right," "Lying Back," and the like.

In response to a posture state detected by the posture state module, IMD 14 may change program group, program, stimulation amplitude, pulse width, pulse rate, and/or one or more other parameters, groups or programs to maintain therapeutic efficacy. When a patient lies down, for example, IMD 14 may automatically reduce stimulation amplitude so that patient 12 does not need to reduce stimulation amplitude manually. In other cases, IMD 14 may automatically increase stimulation amplitude based on posture state. In some cases, IMD 14 may communicate with external programmer 20 to present a proposed change in stimulation in response to a posture state change, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

Referring still to FIG. 1A, a user, such as a clinician or patient 12, may interact with a user interface of an external device, e.g., external programmer 20, to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy changes due to posture changes by patient 12. As another example, a user may select programs or program groups. Again, in the case of electrical stimulation therapy including stimulation pulses, a program may be characterized by an electrode combination, electrode polarities, voltage or current amplitude, pulse width, pulse rate, and/or duration. A group may be characterized by multiple programs that are delivered simultaneously or on an interleaved or rotating basis.

The user interface of external programmer 20 may indicate to the user the posture state in which the patient 12 currently resides. This patient posture state may be a static posture that does not take into account activity level, an activity level that does not take into account posture, or some combination of the posture and activity level that describes the physical position and movement of patient 12. As an example, posture may be characterized as one of the following postures: standing, sitting, lying down on back, lying down on front, lying down on left side, lying down on right side. Activity level may be characterized as one of: high, medium and low, or, e.g., walking, biking, running, or the like.

Posture state may indicate a combination of one of the above postures with one of the above activity levels. For some postures, such as lying down postures, the posture state may not need to consider activity level, as the patient may be less likely to undertake any significant activity in such postures. In other cases, all posture states may take into account posture and activity level, even if there is minimal activity in a particular posture. Posture state may be determined based on detected posture information and/or activity level information generated by a posture state module, which may include one or more accelerometers or other posture or activity level sensors. System 10 may utilize fewer or more different types of posture states depending upon the needs of patient 12.

The patient posture state may be represented by a posture state indication presented to patient 12 and generated by the user interface of programmer 20 as a visible, audible, or tactile indication. When presented as a visible indication, the posture state indication may be, for example, a graphical representation such as, e.g., a symbolic icon, a textual representation (e.g. a word or number), an arrow, or any other type of indication. The visible indication may be presented via a display, such as an a liquid crystal display (LCD), dot matrix display, organic light-emitting diode (OLED) display, touch screen, or the like. In other cases, the visible indication may be provided in a translucent area that is selectively backlit to indicate a posture. An audible indication may be produced by programmer 20 as spoken words stating a posture state, or different audible tones, different numbers of tones, or other audible information generated by the programmer to indicate posture state. A tactile indication may be produced by programmer 20 different numbers of vibratory pulses delivered in sequence or vibratory pulses of different lengths, amplitudes, or frequencies.

Programmer 20 may present multiple indications representative of different patient posture states. IMD 14 may communicate a patient posture state according to a posture state parameter value sensed by a posture state module to external programmer 20, e.g., by wireless telemetry. IMD 14 may communicate the detected posture state, i.e., posture state detection, or a posture state parameter value used to detect the posture state. For example, IMD 14 may transmit a posture state detection to programmer 20 on a periodic, intermittent or continuous basis or in response to a posture state change. Alternatively, programmer 20 may request a posture state detection from IMD 14 on a periodic, intermittent or continuous basis. The posture state detection provided from IMD 14 to programmer 20 may be a posture state value that is interpreted to determined posture state, or simply an indication of the detected posture state, e.g., upright, lying front, lying back, lying left, lying right, or the like. In some examples, programmer 20 may receive a raw signal from an accelerometer used to detect patient posture state, and then detect the patient posture state based on the raw signals transmitted from IMD 14. External programmer 20 then may select and present the associated posture state indication.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use.

As will be described further below, programmer 20 may include a user interface that displays a posture state field representative of a posture state of a patient, display at least one graphical representation representative of at least a portion of a body of the patient, overlays a physiological condition indicator over at least a portion of the graphical representation, and displays at least one of a plurality of therapy parameters that define therapy delivered to the patient. The physiological condition indicator is indicative of a physiological condition of the patient associated with the posture state by the patient. In some examples, therapy information displayed on the user interface of programmer 20 may be transmitted from IMD 14 to programmer 20.

IMD 14 may be constructed with a biocompatible housing, such as titanium or stainless steel, or a polymeric material such as silicone or polyurethane, and surgically implanted at a site in patient 18 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

At the distal tips of leads 16 are one or more electrodes (not shown) that transfer the electrical stimulation from the lead to the tissue. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Figure 1B:
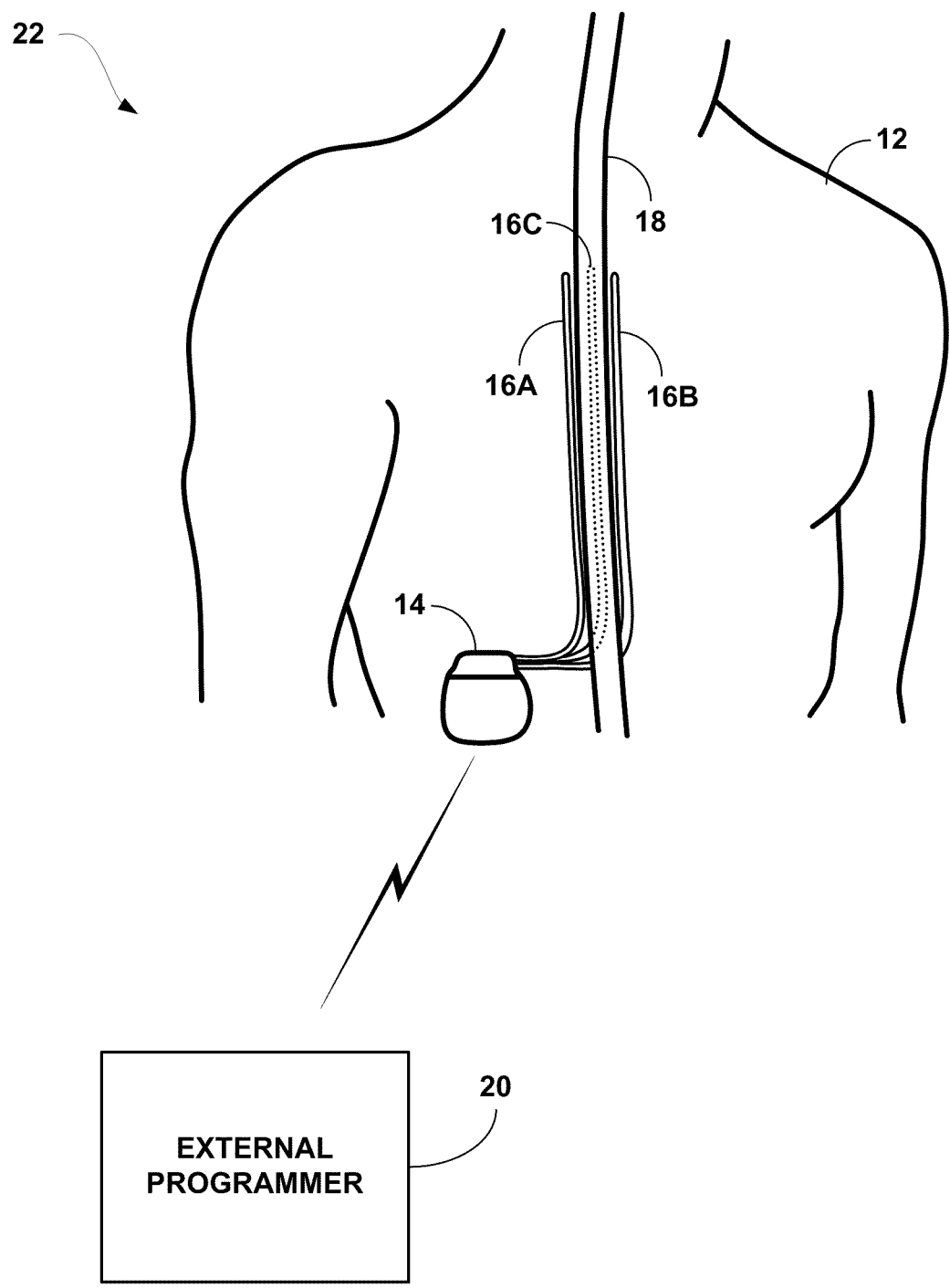
FIG. 1B is a conceptual diagram illustrating an implantable stimulation system including three implantable stimulation leads.

FIG. 1B is a conceptual diagram illustrating an implantable stimulation system 22 including three implantable stimulation leads 16A, 16B, 16C (collectively leads 16). System 22 generally conforms to system 10 of FIG. 1A, but includes a third lead. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. External programmer 20 may be initially told the number and configuration of leads 16 in order to appropriately program stimulation therapy.

For example, leads 16A and 16B could include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible. In some cases, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22.

Figure 1C:
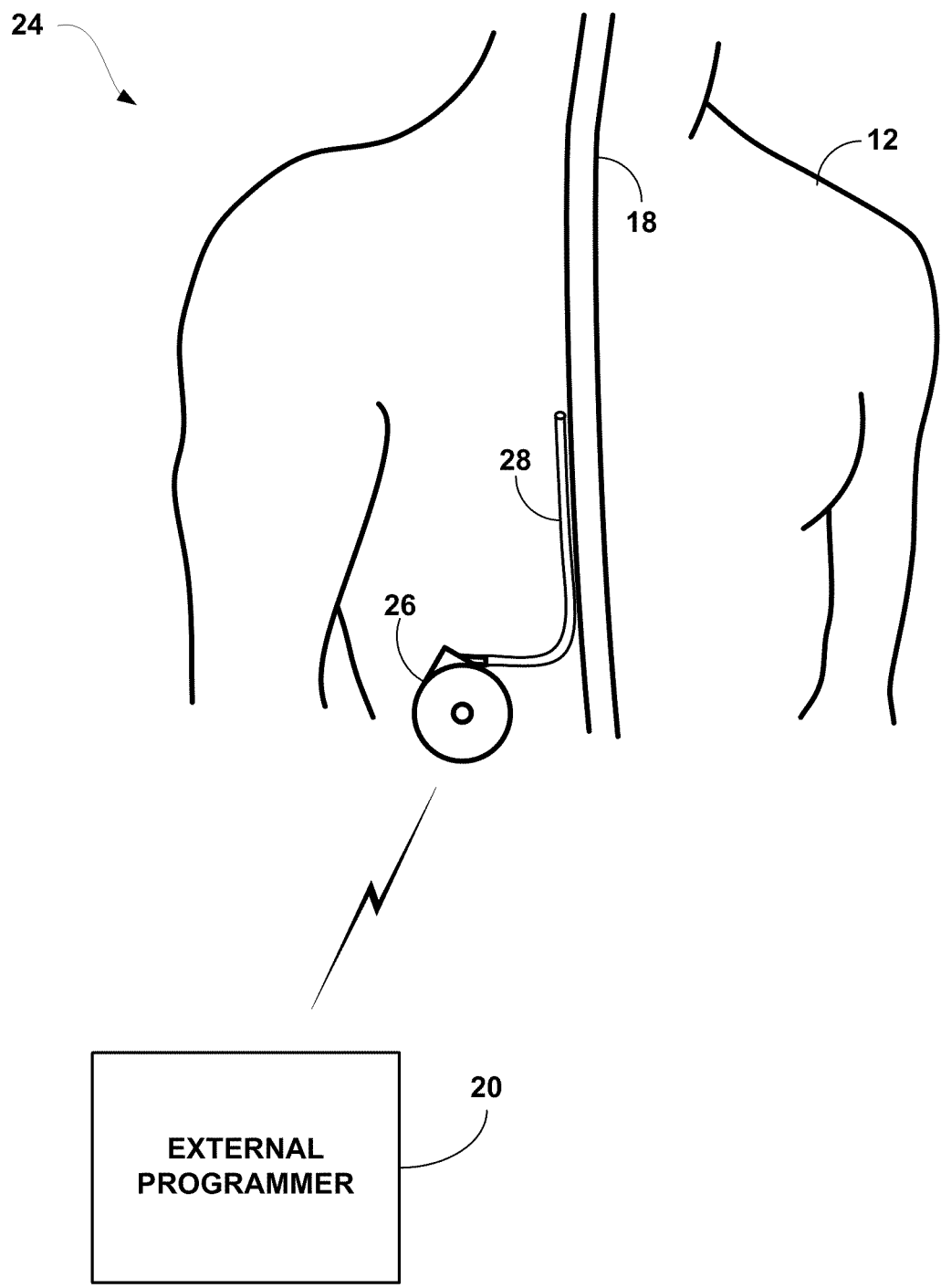
FIG. 1C is a conceptual diagram illustrating an implantable drug delivery system including a delivery catheter.

FIG. 1C is a conceptual diagram illustrating an implantable drug delivery system 24 including one delivery catheter 28 coupled to IMD 26. As shown in the example of FIG. 1C, drug delivery system 24 is substantially similar to systems 10 and 22. However, drug delivery system 24 performs the similar therapy functions via delivery of drug stimulation therapy instead of electrical stimulation therapy. IMD 26 functions as a drug pump in the example of FIG. 1C, and IMD 26 communicates with external programmer 20 to initialize therapy or modify therapy during operation. In addition, IMD 26 may be refillable to allow chronic drug delivery.

Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some embodiments, IMD 26 may be an external device which includes a percutaneous catheter that forms catheter 28 or that is coupled to catheter 28, e.g., via a fluid coupler. In other embodiments, IMD 26 may include both electrical stimulation as described in IMD 14 and drug delivery therapy.

IMD 26 may also operate using therapy parameters that define the method of drug delivery. IMD 26 may include programs, or groups of programs, that define different delivery methods for patient 14. For example, a program that controls delivery of a drug or other therapeutic agent may include a titration rate or information controlling the timing of bolus deliveries. Patient 14 may use external programmer 20 to adjust the programs or groups of programs to regulate the therapy delivery.

Similar to IMD 14, IMD 26 may include a posture state module that monitors the patient posture state. IMD 26 may adjust therapy based on posture state. For example, the posture state module may indicate that patient 12 transitions from lying down to standing up. IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy.

Although examples of therapy information presented by a user interface of an external device, such as, e.g., programmer 20, are described herein primarily with regard to electrical stimulation therapy, examples are not limited as such. For example, the user interface of programmer 20 may present therapy information including a posture state field indicating a patient posture state, as well as patient physiological conditions and therapy parameters associated with the indicated posture state in conjunction with the drug stimulation therapy via IMD 26.

Figure 2:
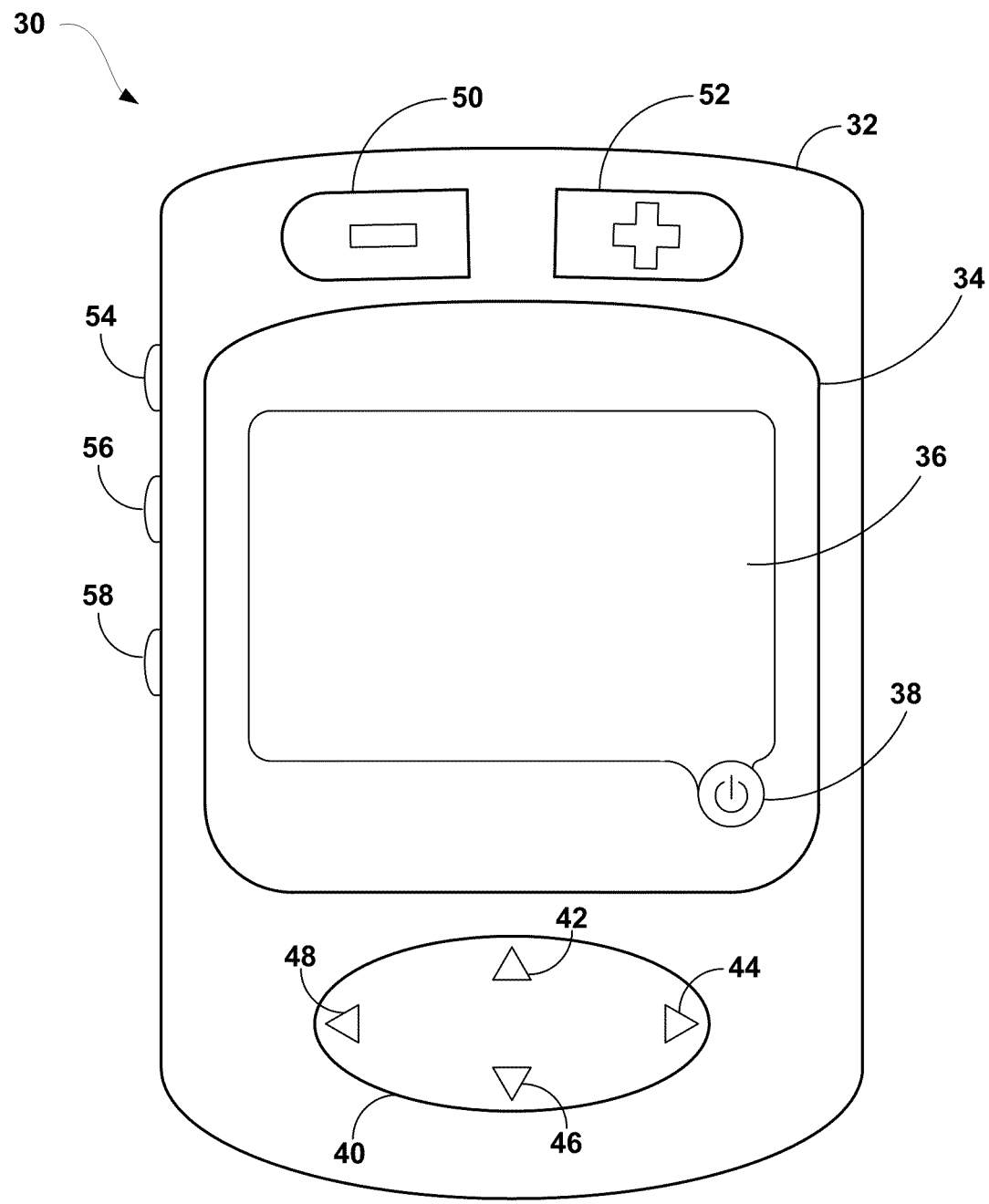
FIG. 2 is a conceptual diagram illustrating an example patient programmer for programming stimulation therapy delivered by an implantable medical device to a patient.

FIG. 2 is a conceptual diagram illustrating an example patient programmer 30 for programming stimulation therapy delivered by an implantable medical device. Patient programmer 30 is an external device and an example embodiment of external programmer 20 illustrated in FIGS. 1A, 1B and 1C and may be used with either IMD 14 or IMD 26. In alternative embodiments, patient programmer 30 may be used with an external medical device. As shown in FIG. 2, patient programmer 30 provides a user interface (not shown) for a user, such as patient 12, to manage and program stimulation therapy. In addition, patient programmer 30 presents a posture state indication to patient 12 in order to represent the patient posture state. Although patient programmer 30 may limit some programming features for patient 12, programmer 30 may display example user interfaces 200, 270, or 290 described herein. Patient programmer 30 is protected by housing 32, which encloses circuitry necessary for patient programmer 30 to operate.

Patient programmer 30 also includes user interface display 36, power button 38, increase button 52, decrease button 50, sync button 58, stimulation ON button 54, and stimulation OFF button 56. Cover 34 protects display 36 from being damaged during use of patient programmer 30. Patient programmer 30 also includes control pad 40 which allows a user to navigate through items displayed on display 36 in the direction of arrows 42, 44, 46, and 48. In some embodiments, the buttons and pad 40 may take the form of soft keys (e.g., with functions and contexts indicated on display 36), with functionality that may change, for example, based on current programming operation or user preference. In alternative embodiments, user interface display 36 may be a touch screen in which patient 12 may interact directly with display 36 without the use of control pad 40 or even increase button 52 and decrease button 50.

In the illustrated embodiment, patient programmer 30 is a hand held device. Patient programmer 30 may accompany patient 12 throughout a daily routine. In some cases, patient programmer 30 may be used by a clinician when patient 12 visits the clinician in a hospital or clinic. In other embodiments, patient programmer 30 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein. Power button 38 may turn patient programmer 30 ON or OFF as desired by patient 12. Patient 12 may control the illumination level, or backlight level, of display 36 by using control pad 40 to navigate through the user interface and increase or decrease the illumination level with decrease and increase buttons 50 and 52, respectively. In some embodiments, illumination of display 36 may be controlled by a knob that rotates clockwise and counter-clockwise. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

User interface display 36 may be a liquid crystal display (LCD), dot matrix display, organic light-emitting diode (OLED) display, touch screen, or similar monochrome or color display capable of providing visible information to patient 12. User interface display 36 may provide a user interface regarding current stimulation therapy, posture state information, provide a user interface for receiving feedback or medication input from patient 12, display an active group of stimulation programs, and display operational status of patient programmer 30 or IMDs 14 or 26. For example, patient programmer 30 may provide a scrollable list of groups, and a scrollable list of programs within each group, via display 36. In addition, display 36 may present a visible posture state indication based on the posture state detection. Further, display 36 may present therapy adjustment information stored during a record mode of IMD 14, in which IMD 14 records posture state transitions, therapy adjustments, or other information, and even present nominal or suggested therapy parameters for a plurality of programs. Patient 12 may then selectively set the plurality of programs to the respective nominal or suggested therapy parameters via a single confirmation input. As described herein, patient programmer 30 may be configured to perform any tasks described with respect to clinician programmer 60 or another external programmer 20. In addition, patient programmer 30 may accept input from patient 12 identifying physiological conditions such as pain or paresthesia that the patient recognizes during therapy or without any therapy being delivered. In some examples, patient may be input a pain score to IMD 14 to identify a relative amount of pain experienced by patient 12.

In some examples, the information provided by patient 12 via programmer 30 may be associated with a posture state of patient 12, e.g., the posture state occupied by patient 12 when the input was received from patient 12, and stored by IMD 14. Such information may include, for example, physiological condition information such as, e.g., pain and/or paresthesia information and/or therapy parameter information, such as, e.g., parameter adjustments received from patient 12. This therapy information may then be presented to a user via interface display 36 with a posture field indicating the posture state of patient 12 that the therapy information is associated with.

Control pad 40 allows patient 12 to navigate through items displayed on display 36. Patient 12 may press control pad 40 on any of arrows 42, 44, 46, and 48 in order to move to another item on display 36 or move to another screen not currently shown on the display. In some embodiments, pressing the middle of control pad 40 may select any item highlighted in display 36. In other embodiments, scroll bars, a scroll wheel, individual buttons, or a joystick may perform the complete or partial functions of control pad 40. In alternative embodiments, control pad 40 may be a touch pad that allows patient 12 to move a cursor within the user interface displayed on display 36 to manage therapy.

Decrease button 50 and increase button 52 provide an input mechanism for patient 12. In general, decrease button 50 may decrease the value of a highlighted stimulation parameter every time the decrease button is pressed. In contrast, increase button 52 may increase the value of a highlighted stimulation parameter one step every time the increase button is pressed. While buttons 50 and 52 may be used to control the value of any stimulation parameter, buttons 50 and 52 may also control patient feedback input. When either of buttons 50 and 52 is selected, patient programmer 30 may initialize communication with IMD 14 or 26 to change therapy accordingly.

When depressed by patient 12, stimulation ON button 54 directs programmer 30 to generate a command for communication to IMD 14 that turns on stimulation therapy. Stimulation OFF button 56 turns off stimulation therapy when depressed by patient 12. Sync button 58 forces patient programmer 30 to communicate with IMD 14. When patient 12 enters an automatic posture response screen of the user interface, pressing sync button 58 turns on the automatic posture response to allow IMD 14 to automatically change therapy according to the posture state of patient 12. Pressing sync button 58 again, when the automatic posture response screen is displayed, turns off the automatic posture response. In the example of FIG. 2, patient 12 may use control pad 40 to adjust the volume, contrast, illumination, time, and measurement units of patient programmer 30.

In some embodiments, buttons 54 and 56 may be configured to perform operational functions related to stimulation therapy or the use of patient programmer 30. For example, buttons 54 and 56 may control the volume of audible sounds produced by patient programmer 30, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, user interface display 36 brightness and contrast, or other similar options. In alternative embodiments, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described herein. Alternative embodiments of patient programmer 30 may include other input mechanisms such as a keypad, microphone, camera lens, or any other media input that allows the user to interact with the user interface provided by patient programmer 30.

In alternative embodiments, the buttons of patient programmer 30 may perform different functions than the functions provided in FIG. 2 as an example. In addition, other embodiments of patient programmer 30 may include different button layouts or different numbers of buttons. For example, patient programmer 30 may even include a single touch screen that incorporates all user interface functionality with a limited set of buttons or no other buttons.

Figure 3:
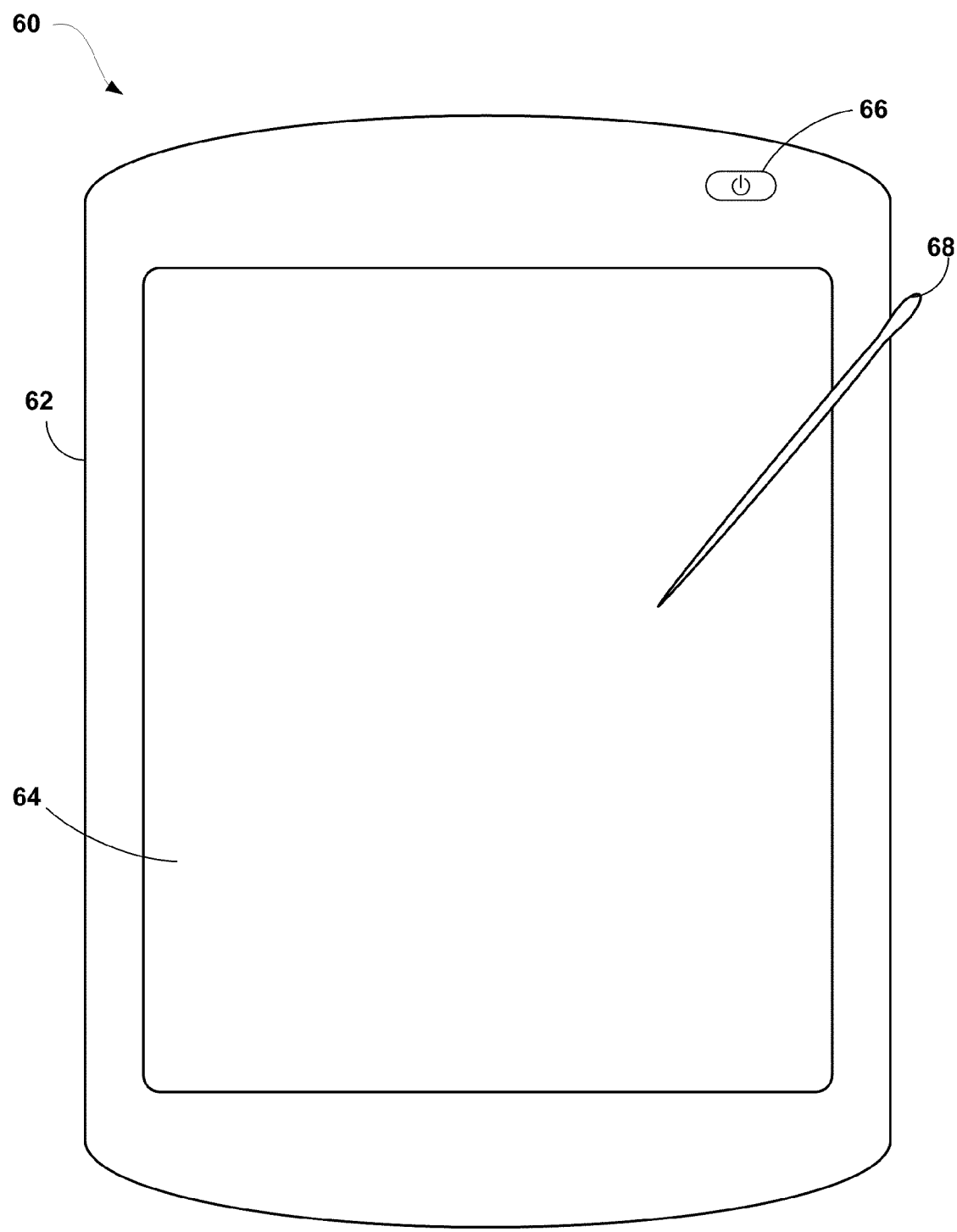
FIG. 3 is a conceptual diagram illustrating an example clinician programmer for programming stimulation therapy delivered by an implantable medical device to a patient.

FIG. 3 is a conceptual diagram illustrating an example clinician programmer 60 for programming stimulation therapy delivered by an implantable medical device. Clinician programmer 60 is an external device and an example embodiment of external programmer 20 illustrated in FIGS. 1A, 1B and 1C and may be used with either IMD 14 or IMD 26. In alternative embodiments, clinician programmer 60 may be used with an external medical device. As shown in FIG. 3, clinician programmer 60 provides a user interface (not shown) for a user, such as a clinician, physician, technician, or nurse, to manage and program stimulation therapy. As described herein clinician programmer 60 may be configured to display any of example user interfaces 200, 270, or 290 described herein. Clinician programmer 60 is protected by housing 62, which encloses circuitry necessary for operation of clinician programmer 60.

Clinician programmer 60 is used by the clinician or other user to modify and review therapy to patient 12. The clinician may define each therapy parameter value for each of the programs that define stimulation therapy. The therapy parameters, such as amplitude, may be defined specifically for each of the posture states that patient 12 will be engaged in during therapy. The clinician may use clinician programmer 60 to define each posture state of patient 12 by using posture cones or other posture volumes, posture zones or other techniques for associating posture state sensor output to the posture state of patient 12. Further, the clinician may use clinician programmer 60 to view real-time therapy information, including posture state data indicating the detected posture state of a patient, for programming stimulation fields or individual stimulation therapy parameters to define therapy for patient 12.

Clinician programmer 60 includes display 64 and power button 66. In the example of FIG. 3, display 64 is a touch screen that accepts user input via touching certain areas within display 64. The user may use stylus 68 to touch display 64 and select virtual buttons, sliders, keypads, dials, or other such representations presented by the user interface shown by display 64. In some embodiments, the user may be able to touch display 64 with a finger, pen, or any other pointing device. In alternative embodiments, clinician programmer 60 may include one or more buttons, keypads, control pads, touch pads, or other devices that accept user input, similar to patient programmer 30.

In the illustrated embodiment, clinician programmer 60 is a hand held device. Clinician programmer 60 may be used within the clinic or on in-house patient calls. Clinician programmer 60 may be used to communicate with multiple IMDs 14 and 26 within different patients. In this manner, clinician programmer 60 may be capable of communicating with many different devices and retain patient data separate for other patient data. In some embodiments, clinician programmer 60 may be a larger device that may be less portable, such as a notebook computer, tablet computer, workstation, or even a remote computer that communicates with IMD 14 or 26 via a remote telemetry device to display example user interfaces 200, 270, or 290.

Most, if not all, of the functions of clinician programmer may be completed via the touch screen of display 64. The user may program stimulation therapy, modify programs or groups, retrieve stored therapy data, retrieve posture state information, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy.

In some cases, all processing may be performed in IMD 14 and distributed to clinician programmer 60 only for presentation to the clinician. Alternatively, two or more of IMD 14, clinician programmer 60, patient programmer 30, or another computing device may share in the processing duties of processing therapy adjustment information and any other data prior to presenting the information on clinician programmer 60.

Housing 62 may be constructed of a polymer, metal alloy, composite, or combination material suitable to protect and contain components of clinician programmer 60. In addition, housing 62 may be partially or completely sealed such that fluids, gases, or other elements may not penetrate the housing and affect components therein. Power button 66 may turn clinician programmer 60ON or OFF as desired by the user. Clinician programmer 60 may require a password, biometric input, or other security measure to be entered and accepted before the user can use clinician programmer 60.

Clinician programmer 60 may take other shapes or sizes not described herein. For example, clinician programmer 60 may take the form of a clam-shell shape, similar to some cellular phone designs. When clinician programmer 60 is closed, at least a portion of display 64 is protected within housing 62. When clinician programmer 60 is opened, one side of the programmer may contain a display while the other side may contain input mechanisms. In any shape, clinician programmer 60 may be capable of performing the requirements described herein.

Figure 4:
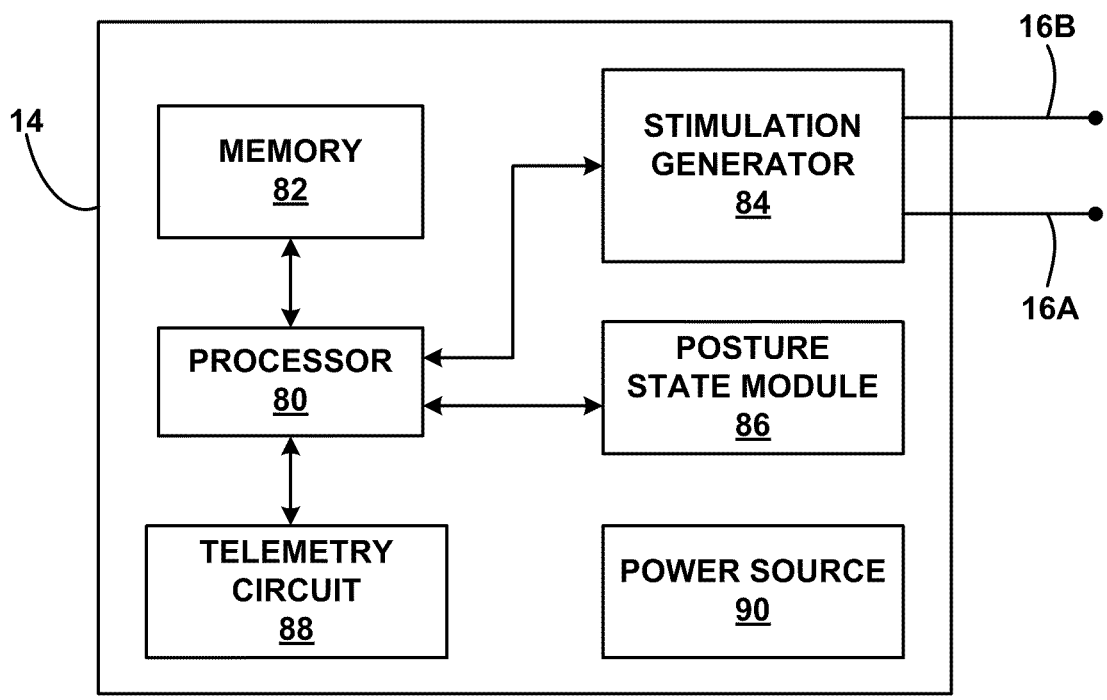
FIG. 4 is a functional block diagram illustrating various components of an example implantable electrical stimulator.

FIG. 4 is a functional block diagram illustrating various components of an IMD 14. In the example of FIG. 4, IMD 14 includes a processor 80, memory 82, stimulation generator 84, posture state module 86, telemetry circuit 88, and power source 90. Memory 82 may store instructions for execution by processor 80, stimulation therapy data, posture state information, posture state indications, and any other information regarding therapy or patient 12. Therapy information may be recorded for long-term storage and retrieval by a user, and the therapy information may include any data created by or stored in IMD 14 via memory 82. Examples of therapy information may include posture state data indicating a posture state of patient 12 detected via posture state module 86, physiological condition information, and therapy parameter information. Memory 82 may include separate memories for storing instructions, posture state information, program histories, and any other data that may benefit from separate physical memory modules.

Memory 82 may be considered, in some examples, a non-transitory computer-readable storage medium comprising instructions that cause one or more processors, such as, e.g., processor 80, to implement one or more of the example techniques described in this disclosure. The term "non-transitory" may indicate that the storage medium is not embodied in a carrier wave or a propagated signal. However, the term "non-transitory" should not be interpreted to mean that memory 82 is non-movable. As one example, memory 82 may be removed from IMD 14, and moved to another device. In certain examples, a non-transitory storage medium may store data that can, over time, change (e.g., in RAM).

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Stimulation generator 84 may include stimulation generation circuitry to generate stimulation pulses or waveforms and switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other embodiments, stimulation generator 84 may include multiple current sources to drive more than one electrode combination at one time. In this case, stimulation generator 84 may decrease current to the first electrode combination and simultaneously increase current to the second electrode combination to shift the stimulation therapy.

An electrode combination may be represented by a data stored in a memory location, e.g., in memory 82, of IMD 14. Processor 80 may access the memory location to determine the electrode combination and control stimulation generator 84 to deliver electrical stimulation via the indicated electrode combination. To change electrode combinations, amplitudes, pulse rates, or pulse widths, processor 80 may command stimulation generator 84 to make the appropriate change or changes to therapy according to instructions within memory 82 and rewrite the memory location to indicate the changed therapy. In other embodiments, rather than rewriting a single memory location, processor 80 may make use of two or more memory locations.

When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12.

According to some examples described herein, such stimulation parameters may be adjusted to modify stimulation therapy delivered by IMD 14 based on the detected posture state of patient 12. In some examples, processor 80 may detect a posture state of patient 12 via posture state module 86 that indicates that a modification of the stimulation therapy is appropriate, e.g., according to instructions stored in memory 82. Processor 80 may access instructions for modifying the stimulation therapy based on the patient 12 posture state, e.g., by changing from a stimulation program appropriate for the previous posture state to a stimulation program appropriate for patient's current posture state.

An exemplary range of electrical stimulation parameters likely to be effective in treating chronic pain, e.g., when applied to spinal cord 18, are listed below. However, other parameter values are contemplated. While stimulation pulses are described, stimulation signals may be of any of a variety of forms such as sine waves or the like.

Pulse Rate: between approximately 0.5 Hz and 1200 Hz, more preferably between approximately 5 Hz and 250 Hz, and still more preferably between approximately 30 Hz and 130 Hz.

Amplitude: between approximately 0.1 volts and 50 volts, more preferably between approximately 0.5 volts and 20 volts, and still more preferably between approximately 1 volt and 10 volts. In other embodiments, a current amplitude may be defined as the biological load in the voltage that is delivered. For example, the range of current amplitude may be between 0.1 milliamps (mA) and 50 mA.

Pulse Width: between about 10 microseconds and 5000 microseconds, more preferably between approximately 100 microseconds and 1000 microseconds, and still more preferably between approximately 180 microseconds and 450 microseconds.

In other applications, different ranges of parameter values may be used. For deep brain stimulation (DBS), as one example, alleviation or reduction of symptoms associated with Parkinson's disease, essential tremor, epilepsy or other disorders may make use of stimulation having a pulse rate in the range of approximately 0.5 to 1200 Hz, more preferably 5 to 250 Hz, and still more preferably 30 to 185 Hz, and a pulse width in the range of approximately 10 microseconds and 5000 microseconds, more preferably between approximately 60 microseconds and 1000 microseconds, still more preferably between approximately 60 microseconds and 450 microseconds, and even more preferably between approximately 60 microseconds and 150 microseconds. Amplitude ranges such as those described above with reference to SCS, or other amplitude ranges, may be used for different DBS applications. Parameter values other than those described above are contemplated.

Processor 80 accesses stimulation parameters in memory 82, e.g., as programs and groups of programs. Upon selection of a particular program group, processor 80 may control stimulation generator 84 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processor 80 also may control telemetry circuit 88 to send and receive information to and from external programmer 20. For example, telemetry circuit 88 may send information to and receive information from patient programmer 30.

Posture state module 86 allows IMD 14 to sense or detect the current patient posture state, e.g., posture, activity or any other static position or motion of patient 12. In the example of FIG. 4, posture state module 86 may include one or more accelerometers, such as three-axis accelerometers, capable of detecting static orientation or vectors in three-dimensions. The three-axis accelerometer may be a micro-electro-mechanical accelerometer. In other examples, posture state module 86 may alternatively or additionally include one or more gyroscopes, pressure transducers or other sensors to sense the current posture state occupied by patient 12. Posture state information generated by posture state module 86 and processor 80 may correspond to an activity and/or posture undertaken by patient 12 or a gross level of physical activity, e.g., activity counts based on footfalls or the like.

Posture state information from posture state module 86 may be stored in memory 82 for later review by a clinician, used to adjust therapy, present a posture state indication to patient 12 and/or clinician, e.g., via user interface display of external programmer 20, or some combination thereof. As an example, processor 80 may record the posture state parameter value, or output, of the 3-axis accelerometer and assign the posture state parameter value to a certain predefined posture indicated by the posture state parameter value. In this manner, IMD 14 may be able to track how often patient 12 remains within a certain posture state. IMD 14 may also store which group or program was being used to deliver therapy when patient 12 was in the sensed posture state. Further, processor 80 may also adjust therapy for a new posture state when posture state module 86 indicates that patient 12 has in fact changed postures. Therefore, IMD 14 may be configured to provide posture responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

Memory 82 may include definitions for each posture state of patient 12. In one example, the definitions of each posture state may be illustrated as a cone in three-dimensional space. Whenever the posture state parameter value, e.g., a vector, from the three-axis accelerometer of posture state module 86 resides within a predefined cone or volume, processor 80 indicates that patient 12 is in the posture state of the cone or volume. In other examples, a posture state parameter value from the 3-axis accelerometer may be compared to values in a look-up table or equation to determine the posture state in which patient 12 currently resides. Examples techniques for detecting a patient posture state include examples described in U.S. patent application Ser. No. 12/433,623, titled "REORIENTATION OF PATIENT POSTURE STATES FOR POSTURE-RESPONSIVE THERAPY," filed Apr. 30, 2009, the entire content of which is incorporated by reference herein.

Posture state-responsive stimulation may allow IMD 14 to implement a certain level of automation in therapy adjustments. Automatically adjusting stimulation may free patient 12 from the constant task of manually adjusting therapy each time patient 12 changes posture or starts and stops a certain posture state. Such manual adjustment of stimulation parameters can be tedious, requiring patient 14 to, for example, depress one or more keys of patient programmer 30 multiple times during the patient posture state to maintain adequate symptom control. In some embodiments, patient 12 may eventually be able to enjoy posture state responsive stimulation therapy without the need to continue making changes for different postures via patient programmer 30. Instead, patient 12 may transition immediately or over time to fully automatic adjustments based on posture state.

Although posture state module 86 is described as containing the 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the patient 12 posture state may be determined from multiple activity sensors placed at various locations on or within the body of patient 12.

In some embodiments, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some embodiments, to confirm or reject changes in sensed posture state that may result from vibration, patient travel (e.g., in an aircraft, car or train), or some other false positive of posture state.

In addition, IMD 14 may store patient 12 input regarding perceived physiological conditions (e.g., symptoms) not detectable by any implemented sensors. For example, patient 12 may provide input to patient programmer 30 that indicates where the patient perceives any symptoms and characteristics of that particular type of symptom. Processor 80 may associate this physiological condition information with the currently detected posture state, the stimulation parameters, and/or a time stamp to provide a complete therapy picture to the patient or clinician at a later time. Such information may be stored in memory 82 of IMD 14, the memory of programmer 20, and/or the memory of other device.

Wireless telemetry in IMD 14 with external programmer 20, e.g., patient programmer 30 or clinician programmer 60, or another device may be accomplished by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. Further, telemetry circuit 88 may transmit information, e.g., posture state data, in real-time when communicating to an external device. For posture state data sent in real-time, telemetry circuit 88 may send the most recently detected posture state or a rolling average posture state at a relative high frequency, e.g., at or near the fastest rate supported by the telemetry circuit. As described above, in some examples, raw signal information rather than information regarding the patient posture state detected by posture state module 86 may be transmitted to an external device for analysis by the external device to determine the posture state of patient 12. To support RF communication, telemetry circuit 88 may include appropriate electronic components, such as amplifiers, filters, mixers, encoders, decoders, and the like.

When the posture state parameter value indicates that patient 12 has changed to a different posture state, processor 80 may communicate with patient programmer 30 via telemetry circuitry 88 to indicate the newly detected posture state, i.e., a new posture state detection that indicates the current posture state occupied by patient 12. In this manner, processor 80 may force patient programmer 30 to present a different posture state indication based upon the sensed posture state parameter value of the patient posture state. In particular, processor 80 may transmit a new posture state detection to patient programmer 30 to indicate the currently detected posture state occupied by the patient. Alternatively, processor 80 may periodically or non-periodically send posture state information to patient programmer 30 either unilaterally or in response to a request from patient programmer 30. For example, patient programmer 30 may request the posture state parameter value or currently detected posture state, either of which indicates detected posture state, and independently change the posture state indication when it is appropriate to do so.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some embodiments, power requirements may be small enough to allow IMD 14 to utilize patient motion and implement a kinetic energy-scavenging device to trickle charge a rechargeable battery. In other embodiments, traditional batteries may be used for a limited period of time. As a further alternative, an external inductive power supply could transcutaneously power IMD 14 when needed or desired.

Figure 5:
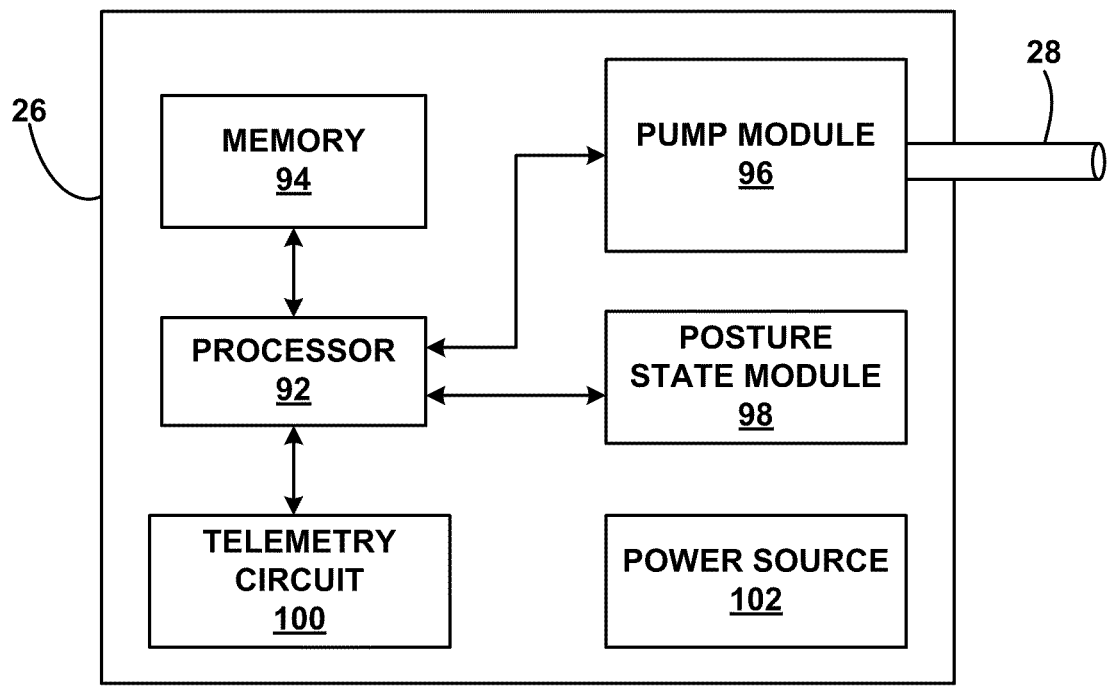
FIG. 5 is a functional block diagram illustrating various components of an example implantable drug pump.

FIG. 5 is a functional block diagram illustrating various components of an IMD 26 that is a drug pump. IMD 26 is a drug pump that operates substantially similar to IMD 14 of FIG. 4. IMD 26 includes processor 92, memory 94, pump module 96, posture state module 98, telemetry circuit 100, and power source 102. Instead of stimulation generator 84 of IMD 14, IMD 26 includes pump module 96 for delivering drugs or some other therapeutic agent via catheter 28. Pump module 96 may include a reservoir to hold the drug and a pump mechanism to force drug out of catheter 28 and into patient 12.

Processor 92 may control pump module 96 according to therapy instructions stored within memory 94. For example, memory 94 may contain the programs or groups of programs that define the drug delivery therapy for patient 12. The therapy programs or groups stored in memory 94 may be associated with one or more postures states of patient, e.g., such that therapy is delivered to patient 12 according to the program(s) or groups(s) associated with the posture state when occupied by a patient. A program may indicate the bolus size or flow rate of the drug, and processor 92 may accordingly deliver therapy. Processor 92 may also use posture state information from posture state module 98 to adjust drug delivery therapy when patient 12 changes posture states, e.g., adjusts their posture.

Figure 6:
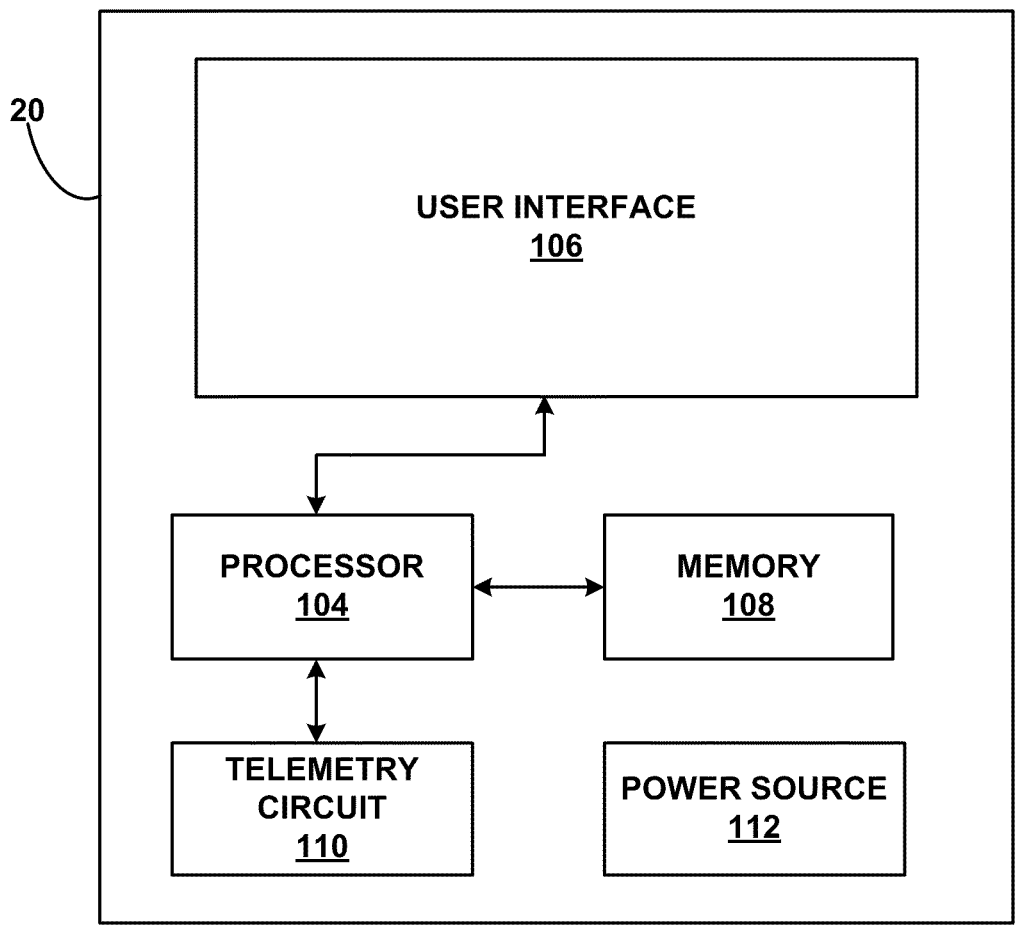
FIG. 6 is a functional block diagram illustrating various components of an example external programmer for an implantable medical device.

FIG. 6 is a functional block diagram illustrating various components of an external programmer 20 for IMDs 14 or 26. As shown in FIG. 6, external programmer 20 is an external device that includes processor 104, memory 108, telemetry circuit 110, user interface 106, and power source 112. External programmer 20 may be embodied as patient programmer 30 or clinician programmer 60. A clinician or patient 12 interacts with user interface 106 in order to manually change the stimulation parameters of a program, change programs within a group, turn posture responsive stimulation ON or OFF, view therapy information, view posture state information, view a posture state indication, or otherwise communicate with IMDs 14 or 26.

User interface 106 may include a screen and one or more input buttons, as in the example of patient programmer 30, that allow external programmer 20 to receive input from a user. Alternatively, user interface 106 may additionally or only utilize a touch screen display, as in the example of clinician programmer 60. As described herein, user interface may be embodied as example user interfaces 200, 270, or 290. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Input buttons for user interface 106 may include a touch pad, increase and decrease buttons, emergency shut off button, and other buttons needed to control the stimulation therapy, as described above with regard to patient programmer 30. Processor 104 controls user interface 106, retrieves data from memory 108 and stores data within memory 108. Processor 104 also controls the transmission of data through telemetry circuit 110 to IMDs 14 or 26. Memory 108 includes operation instructions for processor 104 and data related to patient 12 therapy.

Telemetry circuit 110 allows the transfer of data to and from IMD 14, or IMD 26. Telemetry circuit 110 may communicate automatically with IMD 14 in real-time, at a scheduled time, or when the telemetry circuit detects the proximity of the stimulator. User interface 106 may then update displayed information accordingly. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 14 in addition to programming IMD 14. Alternatively, a recharging device may be capable of communication with IMD 14. Then, the recharging device may be able to transfer programming information, data, or any other information described herein to IMD 14. In this manner, the recharging device may be able to act as an intermediary communication device between external programmer 20 and IMD 14. In other cases, the programmer may be integrated with a recharging functionality in the combined programming/recharging device. The techniques described herein may be communicated between IMD 14 via any type of external device capable of communication with IMD 14.

Figure 7:
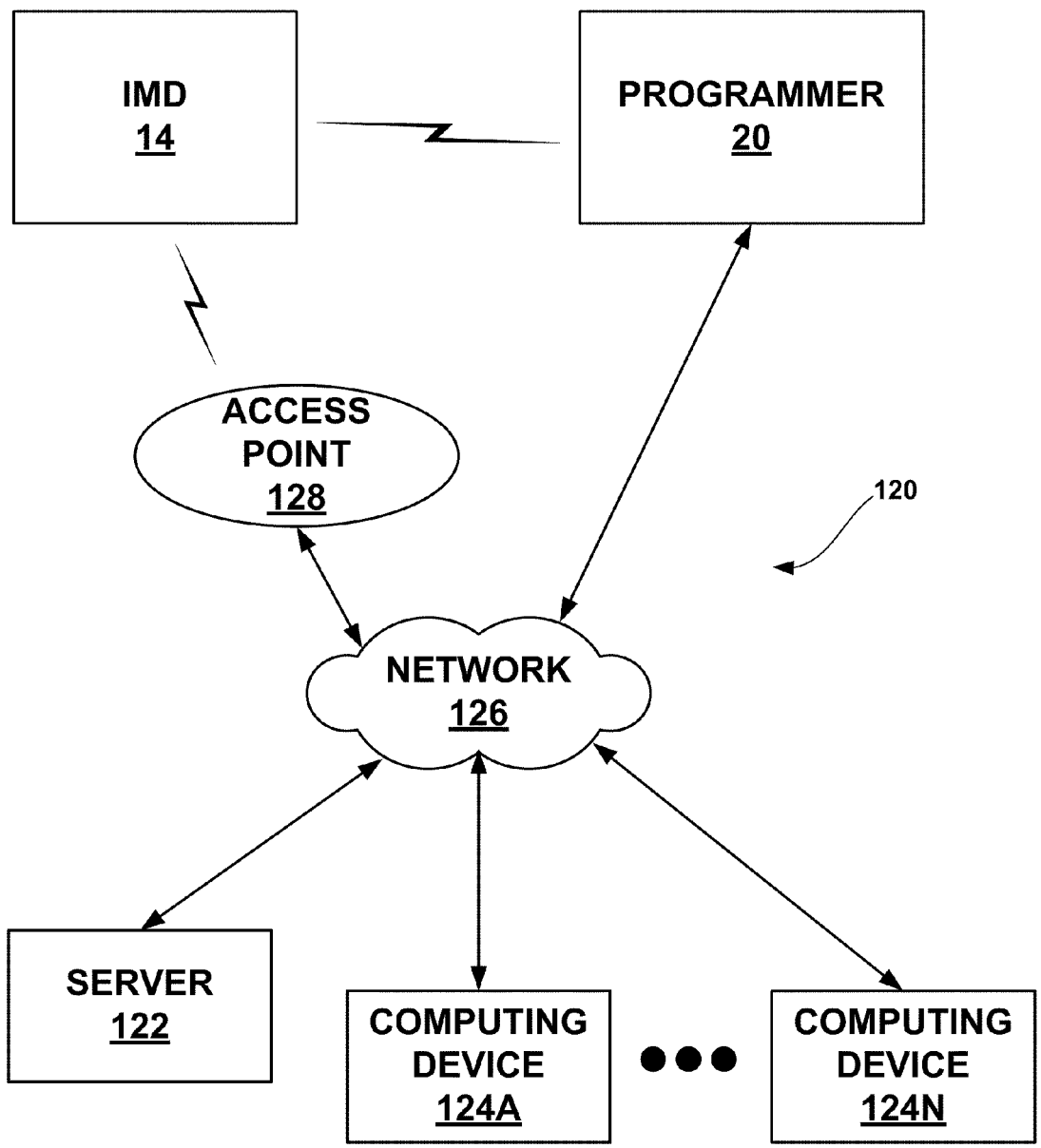
FIG. 7 is a conceptual diagram illustrating an example system that includes an external device, such as a server, and one or more computing devices that are coupled to an implantable medical device and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 to communicate with external programmer 20 via a first wireless connection, and to communication with an access point 128 via a second wireless connection. In other examples, IMD 26 may also be used in place of IMD 14, and external programmer 20 may be either patient programmer 30 or clinician programmer 60.

In the example of FIG. 7, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, digital signal processors (DSPs), application specific integrated circuits (ASICs), field programmable gate arrays (FPGAs), programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other embodiments, access point 128 may be coupled to network 126 through different forms of connections, including wired or wireless connections.

During operation, IMD 14 may collect and store various forms of data. For example, IMD 14 may collect sensed posture state information during therapy that indicate how patient 12 moves throughout each day. In some cases, IMD 14 may directly analyze the collected data to evaluate the patient 12 posture state, such as what percentage of time patient 12 was in each identified posture. In other cases, however, IMD 14 may send stored data relating to posture state information to external programmer 20 and/or server 122, either wirelessly or via access point 128 and network 126, for remote processing and analysis.

For example, IMD 14 may sense, process, trend and evaluate the sensed posture state information and other therapy information. This communication may occur in real time, and network 126 may allow a remote clinician to review the current patient posture state by receiving a presentation of a posture state indication along with other therapy information on a remote display, e.g., computing device 124A. Alternatively, processing, trending and evaluation functions may be distributed to other devices such as external programmer 20 or server 122, which are coupled to network 126. In addition, posture state information and other therapy information may be archived by any of such devices, e.g., for later retrieval and analysis by a clinician. For example, the archived therapy information may be presented to a user via user interface 106 (FIG. 6).

In some cases, IMD 14, external programmer 20 or server 122 may process posture state information or raw data and/or therapy information into a displayable posture state report, which may be displayed via external programmer 20 or one of computing devices 124A-124N. The posture state report may contain trend data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, or any other information relevant to patient 12 therapy, based on analysis and evaluation performed automatically by IMD 14, external programmer 20 or server 122. A clinician or other trained professional may review the historical therapy information including the stimulation parameters, physiological conditions, and posture states to possibly identify any problems or issues with the therapy that should be addressed.

In addition, network 126 may be configured to facilitate real-time communication between IMD 14 and computing device 124A for programming with the current posture state of the patient. Although there may be some slight delay in the transfer of information, this may still be considered real-time programming utilizing any user interface such as user interfaces 200, 270, or 290. The clinician may be able to remotely visit with patient 12, review stored therapy information, and make any programming changes in real-time using system 120.

In some cases, server 122 may be configured to provide a secure storage site for archival of posture state information that has been collected from IMD 14 and/or external programmer 20. Network 126 may comprise a local area network, wide area network, or global network, such as the Internet. In other cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve posture state information and data, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, patient programmer 30, or communicate with patient 12. In an additional example, the clinician may utilize system 120 to monitor multiple patients and share data with other clinicians in an effort to coordinate rapid evolution of effective treatment of patients. Further, posture state detection may also be used to provide notifications, such as providing notification via a wireless link to a care giver that a patient has potentially experienced a fall.

Furthermore, although the disclosure is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating posture state information, as described in this disclosure, may be applied to IMDs that are generally dedicated to sensing or monitoring and do not include stimulation or other therapy components. For example, an implantable monitoring device may be implanted in conjunction with an implantable stimulation device, and be configured to evaluate sensing integrity of leads or electrodes associated with the implantable monitoring device based on sensed signals evoked by delivery of stimulation by the implantable stimulation device.

As described above, in some examples, an external device, such as, e.g., external programmer 20, 30, or 60, may present therapy information to a user via a user interface. The therapy information presented to a user may relate to therapy delivered to a patient by IMD 14, IMD 26, or other medical device. The therapy information presented by the external device may include patient posture state information, physiological therapy information, and therapy parameter information.

The therapy parameter information and physiological therapy information may be associated with patient posture state information. For example, the therapy parameter information presented to a user may include an indicator of one or more therapy parameters programmed for delivery for a particular patient postures state indicated to the user by the user interface. In some examples, the therapy parameter information may include an indicator of previous adjustments made by a user to one or more therapy parameters for therapy delivered to a patient for the associated posture state. In the case of physiological condition information, physiological conditions associated with patient posture state information may include physiological symptoms experienced by the patient when in a particular posture state.

The user interface of an external device may be configured to receive feedback from a user (e.g., a patient or clinician) regarding physiological conditions information and/or the therapy parameter information associated with patient posture state information. In one example, the external device including the user interface for presenting therapy information may receive one or more therapy parameters for the therapy associated with a specific posture state of the patient. Such therapy parameter adjustments may be communicated to IMD 14 or other device for delivering therapy to patient 12 for the associated posture state. In another example, the external device including the user interface for presenting the therapy information may receive input regarding one or more physiological conditions indicated by a patient for a particular posture state. The therapy information presented to a user may be updated based on the input received from a user via the user interface.

Figure 8:
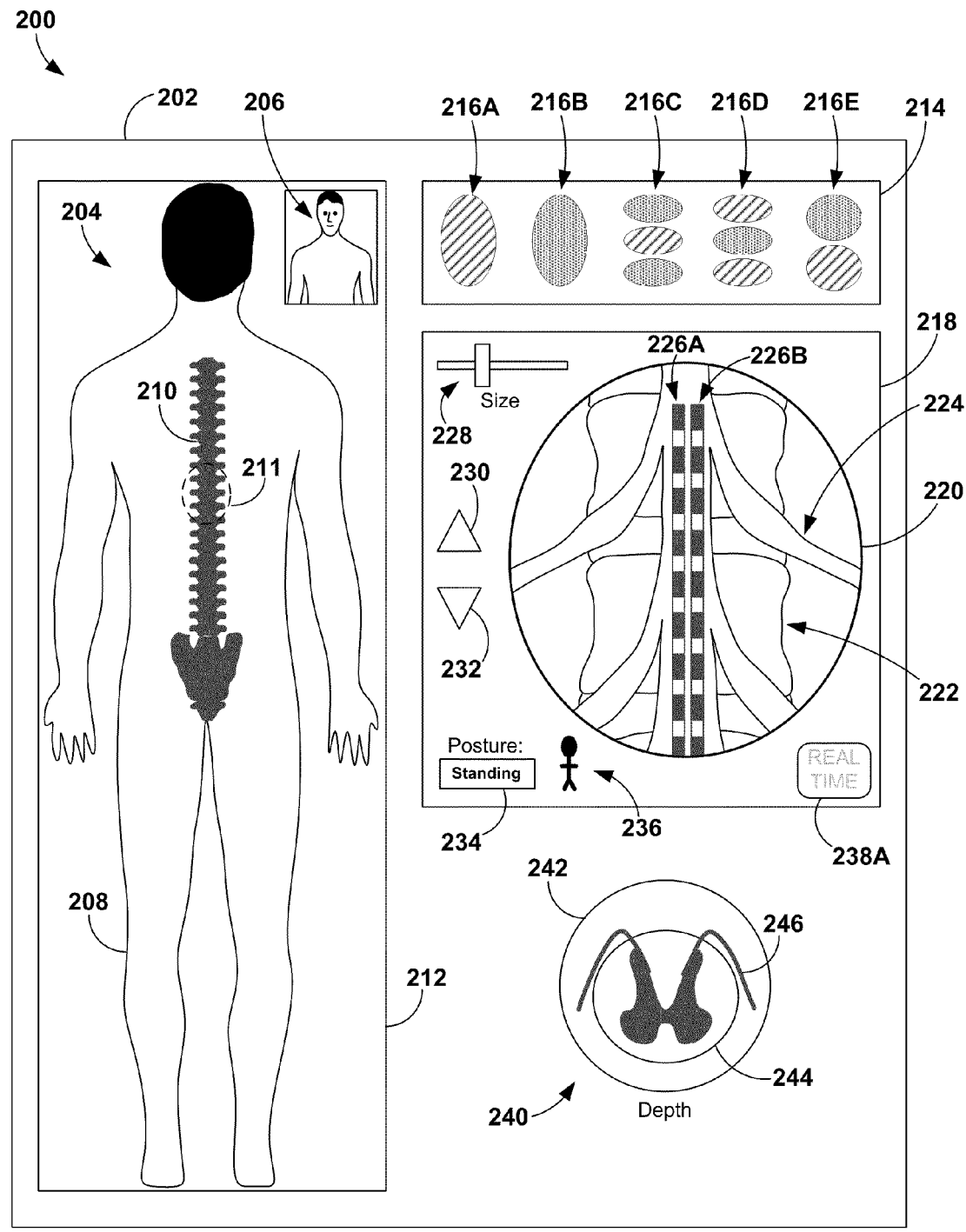
FIG. 8 is a conceptual diagram illustrating an example user interface for displaying example therapy information to a user.

FIG. 8 is a conceptual diagram illustrating example user interface 200 for presenting therapy information to a user on an external device, such as programmer 60 (FIG. 3). Screen 202 of user interface 200 includes avatar window 212, stimulation toolbar 214, programming window 218, and axial view 240 for displaying different therapy information. Although the user of screen 202 may typically be a clinician, patient 12 or other users may also be allowed to interact with screen 202. For ease of illustration, some examples of this disclosure, such as the example of FIG. 8, are described with regard to the presentation of a graphical representation of all or a portion of the body of patient 12 in the form of an avatar, such as, e.g., avatar 204. However, examples are not limited to the presentation of an avatar but may include any graphical representation representative of all and/or a portion of the body of patient 12, e.g., to allow one or more patient physiological conditions to be visually conveyed to a user via an external display device.

Avatar window 212 includes avatar 204, reverse view 206, body surface 208 and spine 210. Avatar 204 is a graphical representation of patient 12 and is intended to provide relative physiological locations for symptoms and/or other physiological conditions of patient 12 and other location specific data. Body surface 208 outlines the exterior of avatar 204 and approximates the body surface of patient 12. Spine 210 is provided to aid the user as a landmark within body surface 208 and indicates the location of the spinal cord within avatar 204. Typically, avatar 204 may include a standard body surface 208 that can be generic to gender, height, weight, etc. However, user interface 200 may incorporate an avatar 204 that is specific to patient 12. The specific avatar may be selected from a library of physical features, created by free hand from a user, generated from photograph, or generated from any type of medical imaging technique already taken of patient 12. Reverse view 206 illustrates the opposite side of avatar 204 and may accept interaction in some embodiments. For example, a user may select reverse view 206 to "flip" avatar 204 to a front view perspective as opposed to the back view perspective of body represented by avatar 204 shown in FIG. 8. In this sense, reverse view 206 may function as a control button that permits the user to select different views. When avatar 204 presents a front perspective view, reverse view 206 may present a back view perspective. When avatar presents a back perspective view, reverse view 206 may present a front view perspective. In either case, the user may press reverse view 206 to change the perspective of avatar 204, e.g., from front to back, or back to front, as applicable to the current view.

Avatar 204 provides an aide for visualization of the patient's conditions, such as physiological symptoms, or any other characteristics related to therapy. For example, this visualization may include one or more of stimulation parameters, electrode configuration, pain mapping, paresthesia mapping, pain scores, anatomy landmarks, medical images, implantable device locations, or therapy delivery locations. In addition, avatar 204 may be rotated to show other surfaces of body surface 208. Side, frontal, or oblique views of avatar 204 may also be selected by the user. These alternative views may be particularly valuable when treating or eliminating superficial pain. Although avatar 204 represents substantially all of the body of patient 12, in some examples only a portion of the body of patient 12 may be represented by avatar 204. For example, for representation of patient physiological conditions that may be localized to one or more areas of the body of patient 12, avatar 204 displayed by user interface 200 may represent only those areas of the body of patient 12. In some examples, a user may be able to zoom in and out on specific areas of the body of patient 12 to focus on therapy information represented via avatar 204 at particular body areas of patient 12.

Stimulation toolbar 214 includes stimulation field shapes that are graphical icons representing stimulation parameters as stimulation fields. Stimulation field shapes 216A, 216B, 216C, 216D, and 216E (collectively "field shapes 216") are tools that the user can use to program stimulation therapy. In other examples, stimulation toolbar 214 may include more and/or different field shapes depending upon the user's desires or commonly used field shapes for a given therapy. Each one of stimulation field shapes 216 define different types of electrical stimulation in a graphical manner. For example, stimulation field shape 216A defines a cathode and stimulation field shape 216B defines an anode. Stimulation field shapes 216C, 216D, and 216E define different combinations of cathodes and anodes. When the user wants to change stimulation therapy parameters of a currently displayed therapy program, the user can select one of stimulation field shapes 216 and place it on the desired location within programming window 218. Programming window 218 can then be used to alter the placed field shape as desired. Programming with stimulation field shapes 216 may reduce the complexity of programming, e.g., as compared to programming of therapy using individual stimulation parameters.

Programming window 218 facilitates viewing of a currently delivered stimulation therapy and/or altering of the stimulation therapy. Programming window 218 includes target view 220, size control 228, location arrows 230 and 232, posture fields 234 and 236, and real-time indicator 238A. Target view 220 displays the target anatomy for stimulation and includes vertebrae 222, dorsal roots 224, and leads 226A and 226B (collectively "leads 226") over the spinal cord. Each darker rectangle of leads 226 illustrates a different electrode of each lead. Any of field shapes 216 may be placed within target view 220 and in relation to electrodes of leads 226 to affect the spinal cord. Leads 226 may be visual representations of leads 16 of FIG. 1A. Size control 228 increases and decreases the size of field shapes within target view 220, while location arrows 230 and 232 allow the user to navigate target view 220 along the length of leads 226.

In some examples, view selector 211 overlaid on avatar 204 may communicate the anatomical location of patient shown in target view 220 with respect to avatar 208. Target view 220 may facilitate the visualization of the position of leads 226 and lead electrodes in relation to the anatomical features of patient 12 at or near the implant site. Target view 220 may display target anatomy any number of different ways. For example the target anatomy may be computer generated graphics, cartoon images, or medical images of patient 12. In other examples, the user may be able to zoom in or out from the target anatomy or even change between different views off the target anatomy. Further, the user may select the desired tools available in programming window 218.

In some examples, the image shown in target view 220 may be a conceptual representation of the leads and anatomical features of patient 12 based on the actual implant location of leads 226. In other examples, the image shown in target view 220 may include a actual medical image such as a fluoroscopic image showing the anatomy of patient 12 and/or the position of leads 226 within patient 12. As the position of leads 226 within patient 12 may change based on the posture state of patient 12, the image shown in target view 220 may change to reflect the position of leads 226 relative to vertebrae 222 or other anatomical location for different patient posture states. In some examples, the image shown in target 220 may reflect the position of leads 226 relative to an anatomical location for the posture state concurrently indicated in posture state fields 234 and 236.

Axial view 240 provides additional information to the user regarding the penetration of the stimulation therapy indicated in target view 220. Axial view 240 includes surrounding tissue 242, spinal cord 244, and dorsal roots 246. When a stimulation field is generated by the field shapes placed within target view 220, user interface 200 generates a projected stimulation depth towards spinal cord 244. The user can then adjust the field shapes in target view 220, and the resulting stimulation field, to the desired depth of spinal cord 244.

In addition, programming window 218 may display posture fields 234 and 236 to indicate a posture state of the patient 12. In the example of FIG. 8, real-time indicator 238A is not highlighted to designate that the real-time connection with IMD 14 is not enabled. If real-time indicator 238 is active to designate real-time connectivity with IMD 14, the highlighted real-time indicator 238B tells the user that posture fields 234 and 236 are indicating the posture state of patient 12 presently detected by posture state module 86 of IMD 14. Posture field 234 is a text box that uses words to designate the posture state. Posture field 236 uses a graphical icon to designate the posture state. In some examples, posture field 236 may indicate a general posture such as lying down while posture field 234 indicates a specific lying down posture such as lying on the back. Although both posture fields 234 are provided in screen 202, other screens of user interface 200 may only include one type of posture field. User interface 200 may allow the user to select the posture field displayed on screen 200.

Screen 202 of user interface 200 is merely one example display of therapy information from IMD 14 or 26. In other examples, the therapy information may be arranged differently or even arranged in multiple screens instead of the one screen of FIG. 8. For example, each of avatar window 212, stimulation toolbar 214, programming window 218, and axial view 240 may be located in difference screens that require the user to navigate to each one separately. In addition, user interface 200 may provide additional information related to the operation of external programmer 20, IMD 14, or the delivery of stimulation therapy.

Figure 9:
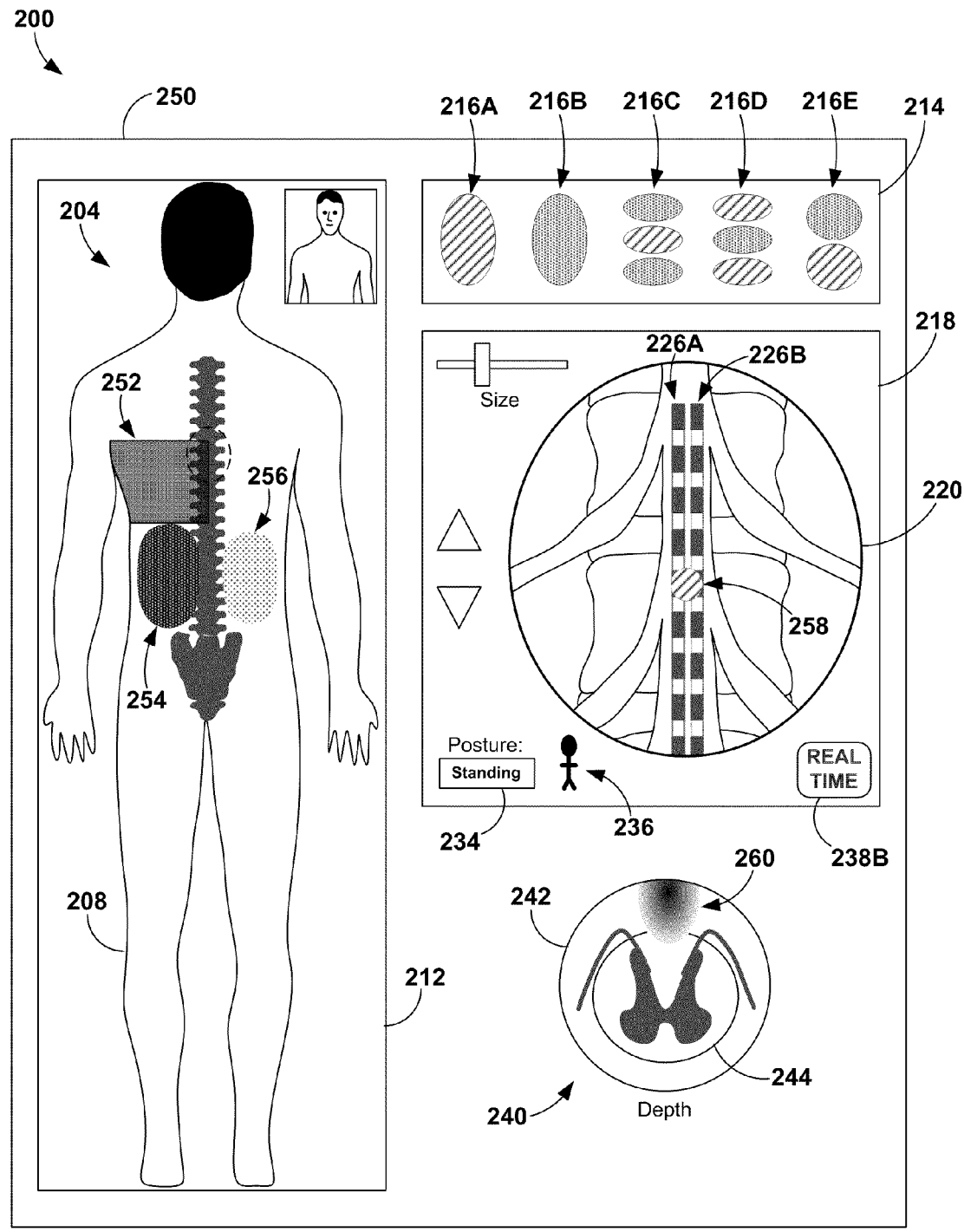
FIG. 9 is a conceptual diagram illustrating an example user interface representing example therapy information such as pain mapping and stimulation fields for a user.

FIG. 9 is a conceptual diagram illustrating example user interface 200 that provides pain mapping and stimulation fields for patient 12 in real-time. As shown in FIG. 9, user interface 200 may provide real-time information to the user with screen 250. Screen 250 is substantially similar to screen 202 of FIG. 8, but screen 250 incorporates actual therapy information into the display. Real-time indicator 238B designates that external programmer 20 is communicating with IMD 14, for example, in real-time. For example, IMD 14 may be transmitting any changes to the detected posture state of patient or therapy substantially simultaneously, or after some nominal delay with the actual occurrence, for display on user interface 200. In the example of FIG. 9, posture fields 234 and 236 indicate that patient 12 is detected in the standing posture state. When updating the posture state of patient in real-time, posture fields 234 and 236 may change to reflect a new patient posture state if IMD 14 detects that patient 12 has entered a new posture state other than that of the standing posture state. While user interface 200 may update the posture state field in real-time, the therapy information associated with the indicated patient posture state may reflect current therapy information or historical therapy information for patient 12. In some cases, a dwell time may be used by the IMD or the programmer to determine that a detected posture state is stable before the posture state is accepted and the posture fields 234, 236 are updated.

Avatar window 212 provides additional information about patient 12 and the current programming process. Physiological condition information in the form of pain region 254 and paresthesia region 256, as identified by patient 12, are overlaid on avatar 204. Patient 12 may define pain and paresthesia regions such as regions 254 and 256 through interaction with patient programmer 30. In some cases, at least a portion of pain and paresthesia regions 254 and 256 may be presented on top of one another as paresthesia may be used to target a region of pain. Pain region 254 and paresthesia region 256 are just two possible physiological condition indicators that may be overlaid on avatar 204. Alternatively, the clinician may outline each pain and paresthesia regions by drawing directly on avatar 204. User interface 200 may then store the defined regions in external programmer 20 for later review. In the example of FIG. 9, pain region 254 indicates that patient 12 is experiencing pain in the lower left back in the standing posture state and the delivery of the current stimulation therapy. In addition, patient 12 is experiencing paresthesia, or tingling caused by stimulation therapy, in the lower right back area of pain region 256. Pain regions and paresthesia regions are included in pain mapping, one of the various ways that the user can interact with avatar 204.

During the programming process, the clinician may interact with avatar 204 to adjust stimulation therapy and minimize any pain regions. As shown in FIG. 9, the clinician has selected active region 252 as the area of avatar 204 to treat with stimulation therapy. Accordingly, programming window 218 displays the target anatomy within target view 220. Leads 226 are shown over the spinal cord. In addition, stimulation field 258 indicates the current stimulation therapy provided to the spinal cord. Depth field 260 in axial view 240 indicates the depth of the stimulation field in relation to spinal cord 244. Depth field 260 in axial view 240 may change depending on the patient posture state indicated by posture state fields 234 and 236. Such changes may be consistent with actual changes in the stimulation field relative to the spinal cord of patient 12 when occupying particular posture states. For example, depth field 260 may move closer to spinal cord 244 to represent compression of a lead toward the spinal cord of patient 12 when patient 12 enters a lying posture. In this manner, a user may be able to visualize the stimulation field for each posture state and assist the user in programming therapy for the patient 12 in view of such information.

In screen 250, the clinician may choose one or more field shapes 216 from stimulation toolbar 214 and drag them into target view 220 to change the stimulation field delivered to patient 12. Once the clinician has made any changes, external programmer 20 may communicate in real-time with IMD 14, for example, to upload the new stimulation parameters and adjust the delivered therapy. In this manner, the clinician may work with the patient in real-time to identify effective stimulation fields that minimize pain region 254. Alternatively, only posture state data may be transferred in real-time and the clinician may need to close the programming session before new stimulation parameters and/or physiological condition information is uploaded to IMD 14.

If the clinician desires to continue programming or viewing the current programs that define stimulation therapy, patient 12 may assume different posture states while the clinician reviews the therapy information. When real-time communication is activated, posture fields 234 and 236 will change according the posture state of patient 12 currently detected by posture state module 86 of IMD 14. If posture fields 234 or 236 do not indicate the correct posture state of patient 12, the clinician may navigate to another screen of user interface 200 to calibrate posture state module 86. In some examples, calibration of posture state module 86 may also occur in real-time.

FIGS. 10A-D are conceptual illustrations of posture icons that represent patient posture states. Posture icons 237A, 237B, 237C, and 237D (collectively "posture icons 237") are graphical icons that may be presented by user interface 200, for example, in posture field 236. Multiple different graphical icons are needed to indicate the different posture states that patient 12 may be engaged in during therapy. Posture field 236 may display any graphical icon, graphical representation, symbolic representation, an arrow, or any other type of indication of patient posture state.

Figure 10A:
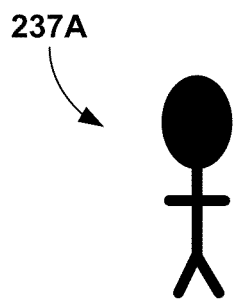
FIGS. 10A-D are conceptual illustrations of example posture icons that are indicative of patient posture states.
Figure 10B:
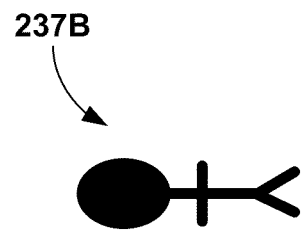
Figure 10C:
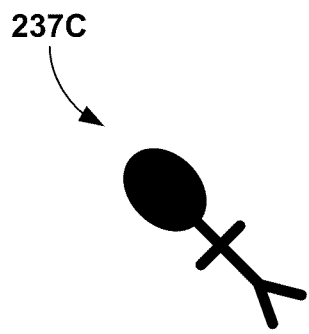
Figure 10D:
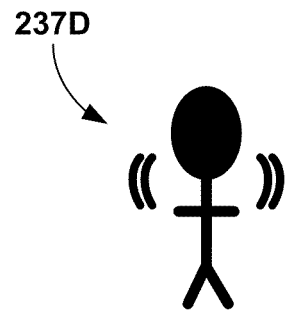

FIG. 10A shows posture icon 237A to represent patient 12 standing upright. FIG. 10B shows posture icon 237B to represent patient 12 lying down horizontally. FIG. 10C shows posture icon 237C to represent patient 12 in a reclining position. Posture icon 237C may be displayed when patient 12 is sitting down in a chair, for example. In addition, FIG. 10D shows posture icon 237D to represent that patient 12 is engaged in some kind of activity. For example, posture icon 237D may be displayed when patient 12 is running, walking, or even riding in a car. Posture state module 86 may detect this activity any time that the frequency of changing acceleration is above a predefined threshold or a predefined range.

Posture icons 237 are merely examples of graphical icons that could be displayed by user interface 200 to indicate the posture state of patient 12. In other examples, posture icons 237 may be detailed to show more human features, simplified to show only the head of patient 12, or even a scaled down version of avatar 204. In any case, posture icons 237 are displayed according to the posture state indicated by the therapy information at the particular identified time.

The number of graphical icons needed for display can be limited by the number of different posture states that the posture module can detect. Although only four posture icons 237 are described here, more or fewer posture icons may be used in user interface 200 by external programmer 20. For example, different lying down posture icons may be needed if the posture state module can differentiate between patient 12 lying face down, lying on either side, or lying face up. Further, the posture state module may be capable of differentiating between different types of activities, e.g., walking, running, biking, or swimming.

In addition, posture field 234 of user interface 200 may provide parallel textual representations of any graphical icons displayed in posture field 236. The text may clarify any ambiguous indication by the graphical icons. Further, posture field 234 may provide greater detail about the identified posture state. For example, posture icon 237B may indicate that patient 12 is lying down, but posture field 234 may display "lying left side" to further indicate the specific posture state of patient 12 at that identified time.

Figure 11:
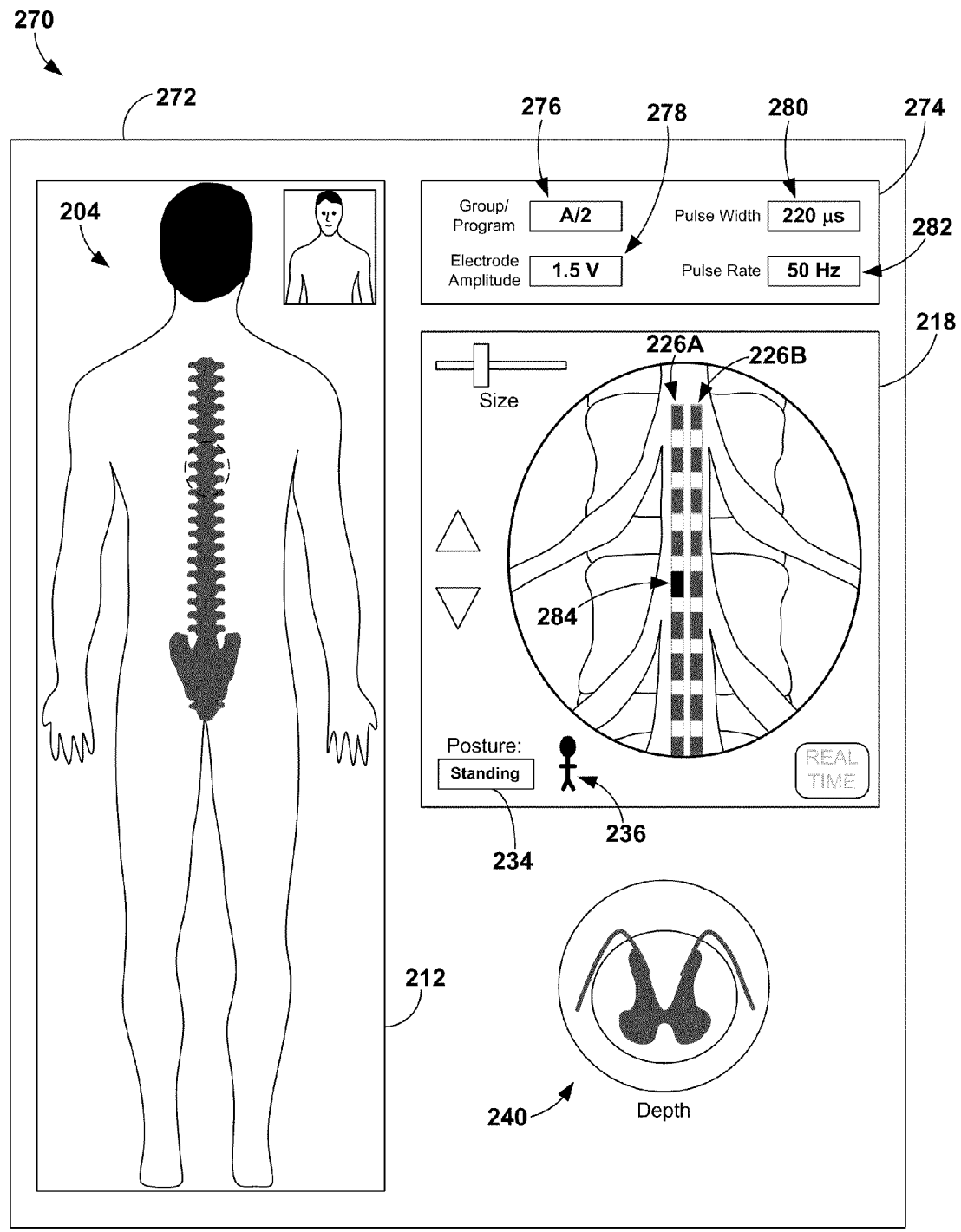
FIG. 11 is a conceptual diagram illustrating an example user interface for displaying stimulation parameters in conjunction with an example avatar of the patient and patient posture state.

FIG. 11 is a conceptual diagram illustrating example user interface 270 for displaying stimulation parameters of the stimulation program in conjunction with avatar 204 of patient 12. User interface 270 is substantially similar to user interface 200 described in FIG. 8. However, user interface 270 displays parameter window 274 instead of stimulation toolbar 214. As shown in FIG. 11, screen 272 of user interface 270 displays parameter window 274 with avatar window 212, programming window 218, and axial view 240. User interface 270 is directed to electrical stimulation, but parameter window 274 could also be configured for drug delivery with IMD 26 in other examples.

Parameter window 274 provides detailed stimulation parameter data for the currently viewed stimulation program that defines the therapy. The stimulation parameter data may correspond to therapy defined for delivery to patient 12 when engaged in the posture state indicated by posture fields 234 and 236. Some users may prefer this display of programming information instead of the graphical field shapes and stimulation fields to viewing and adjusting stimulation therapy. The group letter and program number can be found in program box 276. The group letter indicates to which group of programs the program belongs. The program number indicates which set of stimulation parameters is being used for therapy. In the example of FIG. 11, program "2" of group "A" is being shown. In cases in which IMD 14 incorporates slot-based therapy programming for delivering therapy to patient 12, parameter window 276 may include an indication of a program slot and/or program for the program slot, as well as an indication of therapy parameters values set for the program.

Selected electrode 284 indicates to which electrode of leads 226 the stimulation parameters of parameter window 274 apply. The user may select different electrodes of leads 226 to view those parameters and make any desired changes. Amplitude box 278 displays the amplitude of the selected electrode in the electrode configuration. Here, the amplitude for selected electrode 284 is 1.5 volts. The amplitude displayed in amplitude box 278 may in voltage or current, depending upon what type of electrical stimulation is being provided.

Pulse width box 280 indicates the pulse width of each pulse delivered by selected electrode 284. In addition, pulse rate box 282 indicates the rate or frequency of the pulses delivered by selected electrode 284. Although the values of pulse width box 280 and pulse rate box 282 may be specific to selected electrode 284, these values may be the same for all electrodes of the electrode combination of the program used to deliver stimulation therapy. User interface 270 may display the entire electrode configuration of the program in some embodiments.

Stimulation window 274 may also accept adjustment input from the user to any of the stimulation therapy parameters. The user may simply select one of boxes 278, 280, and 282 and then enter the new parameter value. Upon entering the new stimulation parameter value, user interface 270 may instruct external programmer 20 to adjust the parameter of that program. If the user is merely reviewing stored therapy information, the modified program may be uploaded to IMD 14, for example, for later use. If the user is viewing a current program in real-time programming, external programmer 20 may immediately upload the adjusted parameter to IMD 14 for delivery to patient 12.

In other examples, stimulation parameters for each program may be presented in other ways. For example, each stimulation parameter for all active electrodes in the electrode configuration may be displayed to the user at once. Alternatively, the user may need to navigate to a different screen in order to make desired changes to one or more stimulation parameter values.

Figure 12:
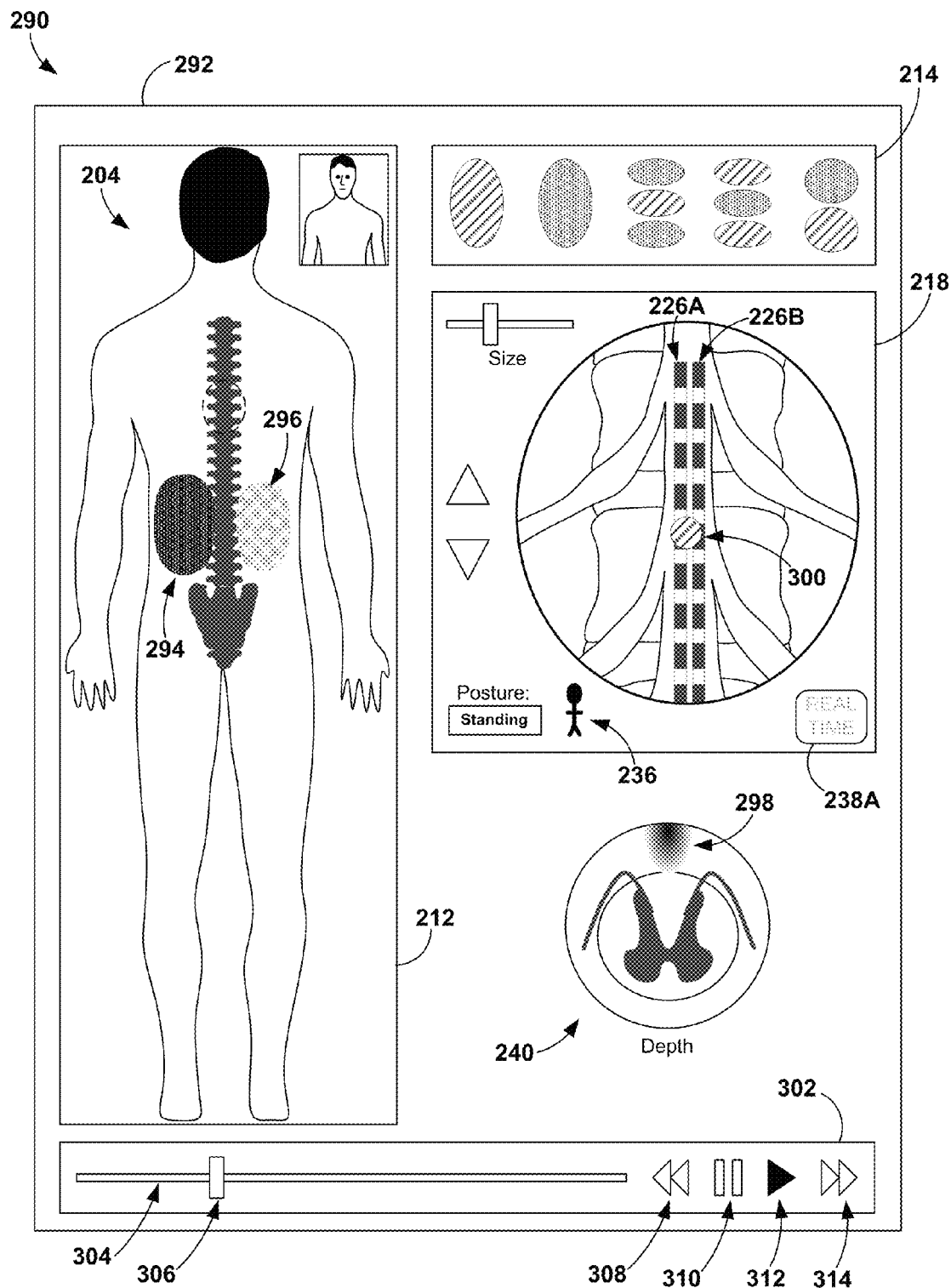
FIGS. 12 and 13 are conceptual diagrams illustrating an example user interface with an example playback field that enables a user to review a sequence of previously stored therapy information over a period of time.
Figure 13:
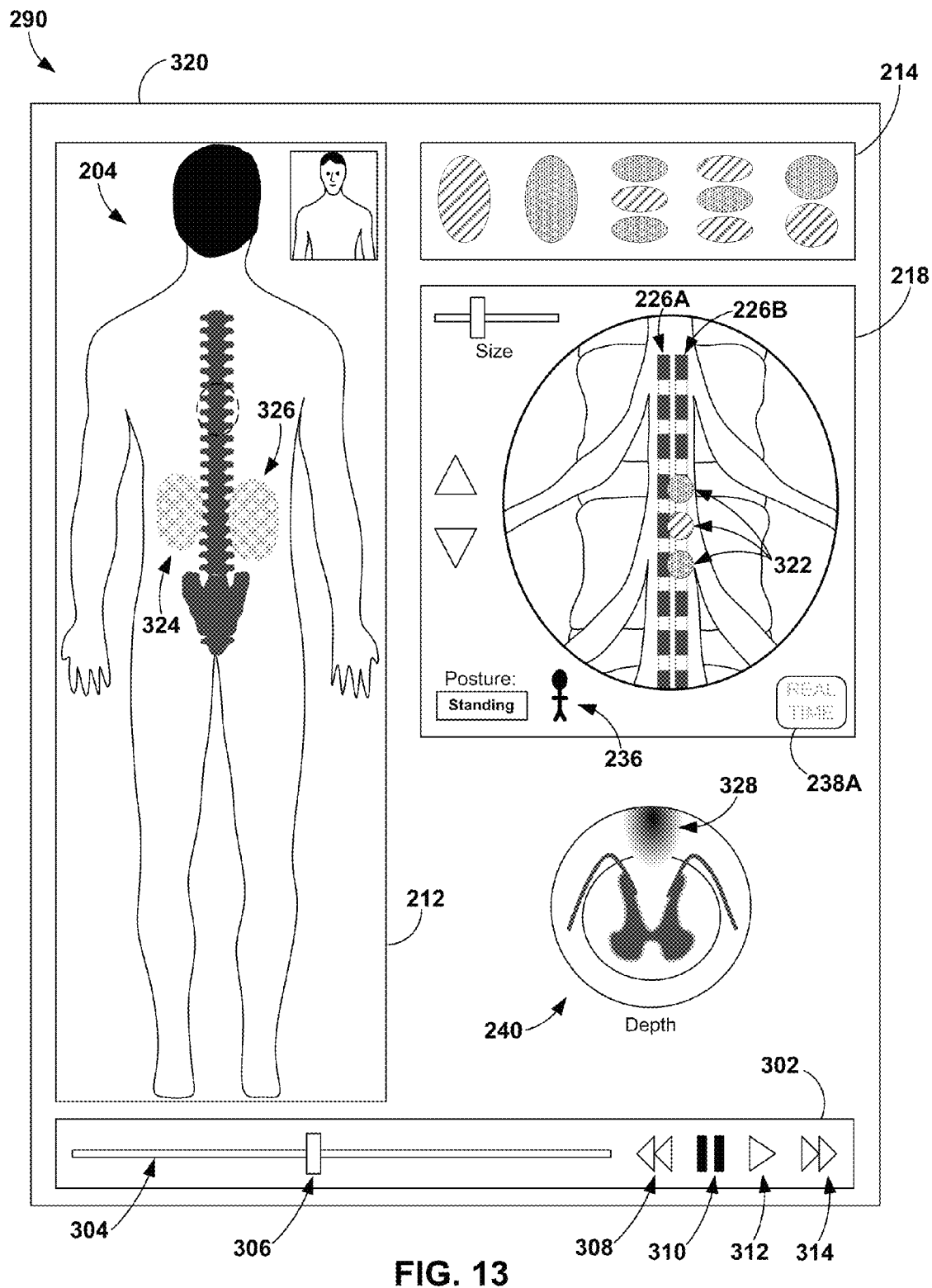

FIGS. 12 and 13 are conceptual diagrams illustrating example user interface 290 with playback field 302 that enables a user to review a sequence of previously stored therapy information over a period of time, which also may be referred to as historical therapy information. User interface 290 is substantially similar to user interface 200 of FIG. 8. However, user interface 290 also includes playback field 302 to facilitate the review of historical therapy information retrieved from the memory of IMD 14 or 26. When in playback mode, real-time indicator 238A is not highlighted to designate that real-time communication is not active. However, in some examples, the posture state of patient 12 may be update in real-time, even though all or a portion of the therapy information associated with the posture state of the patient may reflect historical therapy information.

As shown in FIG. 12, screen 292 of user interface 290 includes playback field 302. Playback field 302 allows the user to interact with any of time bar 304, time position 306, reverse button 308, pause button 310, play button 312, or forward button 314 to select a portion of the therapy information to review. The user can select any point on time bar 304 to force time position 306 to jump to that identified time. The user can also select time position 306 and drag the time position to any desired point along time bar 304. Alternatively, the user can select reverse button 308 to move backward in time or forward button 308 to more forward in time. Each selection of either reverse button 308 or forward button 308 may jump time position 306 a certain amount of time. The jump may be a predetermined amount of time or a percentage of the total time represented by time bar 304.

The user may also select play button 312 to progress sequentially through the therapy information as experienced by patient 12. Although the play mode may move in the real-time of prior events, this play may be too slow for effective review. Therefore, the play move may be an accelerated movement through time, e.g., at a preset pace or according to the total period of therapy information. If the user wants to pause or stop at a certain time point, the user can select pause button 310.

In some examples, specific time periods of interest may be identified by a user for review via user interface 290. For example, when patient 12 experiences an occurrence of interest to the therapy and/or patient condition, patient 12 may indicate the occurrence to IMD 14 or other device, e.g., via programmer 20 or by physically tapping IMD 14, so as to identify the time period of the occurrence. The therapy information from this time period may later review by a user via user interface 290 to analyze details of the therapy information at the time of the occurrence of interest. For example, a patient may identify time of particularly effective or ineffective therapy delivered during at a specific time period. A user may review the therapy information from that time period vie user interface 290 determine the posture state(s) of patient 12 during the time period and/or one or more values of the therapy parameters of the therapy delivered during that time. Such information may, for example, facilitate a user in identifying desirable or undesirable therapy parameter values for particular patient posture states. In some examples, IMD 14 may be configured to store therapy information continuously for historical playback or may be configured to store therapy information upon indication from a user indicating a time period that may be of interest for later review of therapy information during that time period.

As time position 306 moves through the time represented by time bar 304, the therapy information displayed in avatar window 212, programming window 218, and axial depth 240 changes according to the physiological conditions, stimulation therapy parameters, and posture state of patient 12 at that identified time in the past. In the example of FIG. 12, the indicated time of time position 306 is used to display pain region 294 and paresthesia region 296 on avatar 204 as the patient conditions at that time. Correspondingly, stimulation field 300 is displayed on the target anatomy to represent the stimulation therapy delivered to patient 12 at this same time. Depth field 298 indicates the modeled depth of the stimulation as well. Further, the posture state of patient 12 at the identified time is represented as standing in posture field 236. The user could adjust stimulation of the presented program at this time, or the user could continue to move through time as desired.

As shown in FIG. 13, screen 320 of user interface 290 indicates that the user has moved forward in time from the therapy information of FIG. 12. At the identified time of FIG. 13, avatar 204 displays paresthesia regions 324 and 326 while patient 12 was also in the standing posture state as represented in posture field 236. This change in pain mapping on avatar 204 is due to a change in stimulation selected by patient 12 during therapy. For example, paresthesia region 324 may now cover pain region 294 (FIG. 12). As shown in programming window 218, stimulation fields 322 indicate where stimulation is being directed to the target anatomy. Accordingly, depth field 328 indicates a deeper effect of the stimulation field as compared to the previous depth view 298 of FIG. 12. Again, the user may continue to move through time of previous therapy or made adjustments to the stimulation provided to patient 12 at the indicated posture state.

Figure 14:
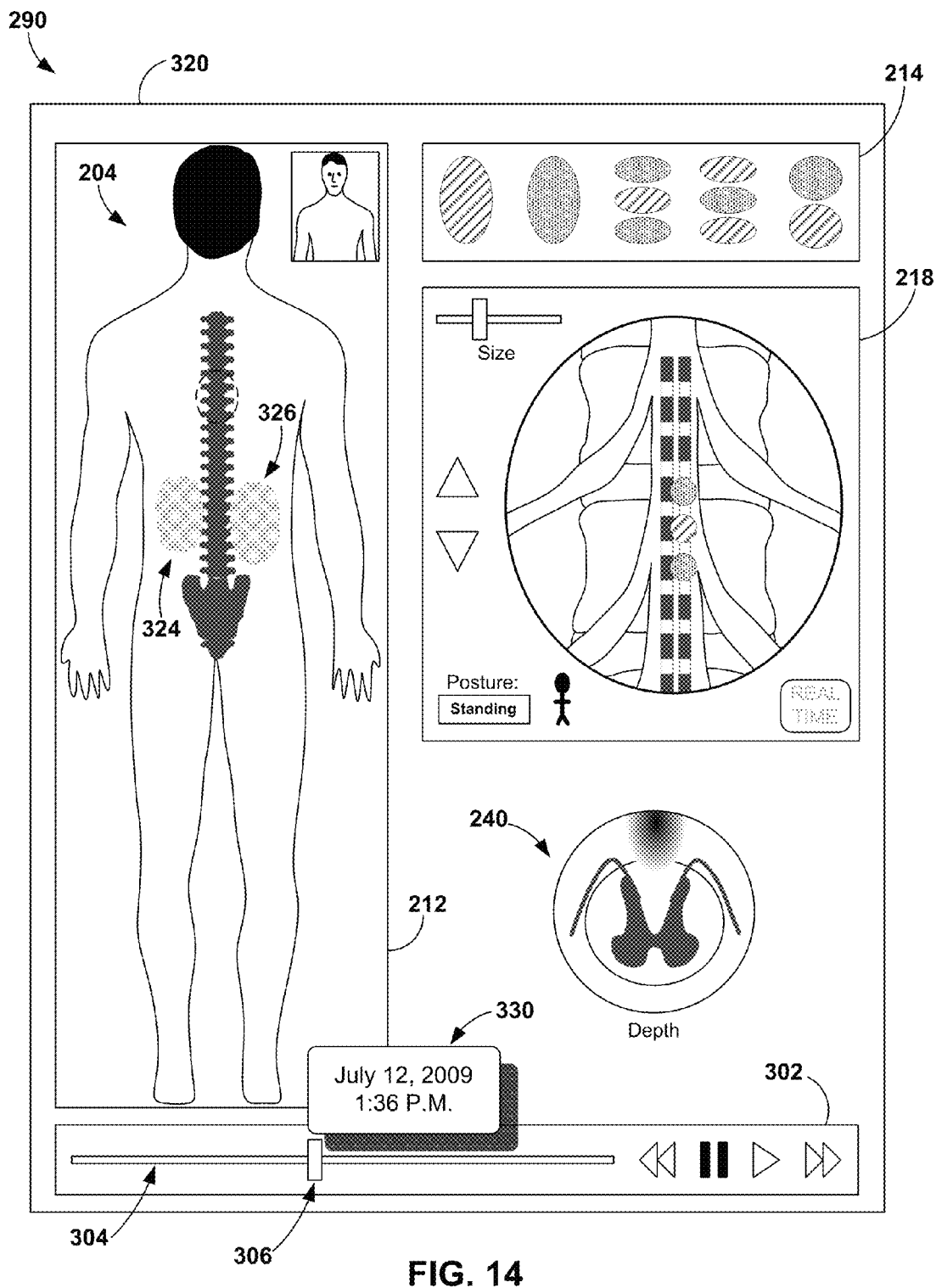
FIG. 14 is a conceptual diagram illustrating an example user interface for displaying an example pop-up window containing detailed time information for previously stored therapy information.

FIG. 14 is a conceptual diagram illustrating example user interface 290 for displaying time pop-up window 330 containing detailed time information. As shown in FIG. 14, user interface 290 provides screen 320 that supports pop-up windows to give more detailed information to the user. Specifically, time pop-up window 330 is displayed by user interface 290 when the user selects or hovers over time position 306. Therefore, time pop-up window 330 indicates that time position 306 and the displayed therapy information were from Jul. 12, 2009 at 1:36 P.M. during patient therapy.

User interface 290 may also support other pop-up windows. For example, the user may desire to view other detailed information from playback field 302. The user may select or hover over time bar 304 to view a pop-up window showing the entire range of time covered by time bar 304. This may include the start and end dates and any gaps in therapy in between. Alternatively, playback field 302 may display this detailed time information at all times without needing a pop-up window. These options may be user selectable from a preference screen of user interface 290.

Figure 15:
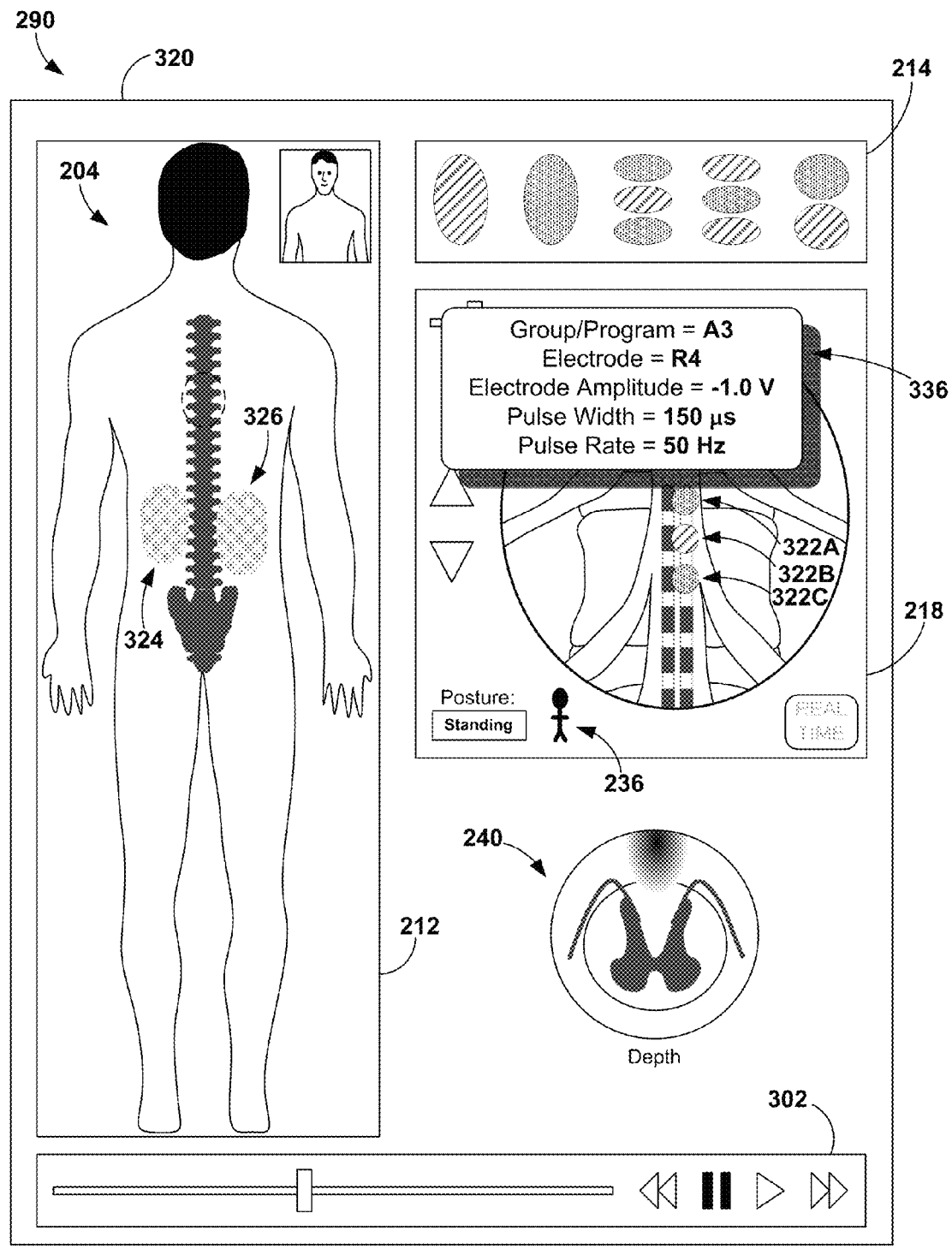
FIG. 15 is a conceptual diagram illustrating an example user interface for displaying a example pop-up window containing detailed stimulation therapy parameter information.

FIG. 15 is a conceptual diagram illustrating example user interface 290 for displaying parameter pop-up window 336 containing details of stimulation therapy parameters. As shown in FIG. 15, user interface 290 provides screen 320 supporting pop-up windows such as that of FIG. 14. Here, parameter pop-up window 336 is displayed by user interface 290 when the user selects or hovers over one of stimulation fields 322A, 322B, 322C (collectively "stimulation fields 322"). Specifically, the user has selected stimulation field 322A. The resulting parameter pop-up window 336 provides the detailed stimulation therapy parameter values for stimulation field 322A. The information of window 336 includes the group and program name, the electrode used, the electrode amplitude, the pulse width, and the pulse rate. The user can select any of other stimulation fields 322 to view similar stimulation parameter values. Parameter pop-up window 336 may disappear when the user selects something else in screen 320 or selects the pop-up window.

Parameter pop-up window 336 allows the user to view stimulation parameter values without cluttering screen 320 with this detailed information at all times. It is noted that parameter pop-up window may also be used in any of user interfaces 200, 270, or any other user interfaces displaying therapy information. Pop-up windows may also be used to provide detailed information regarding the posture state of patient 12. For example, the user may select posture field 236 to view the output of posture state module 86.

Figure 16:
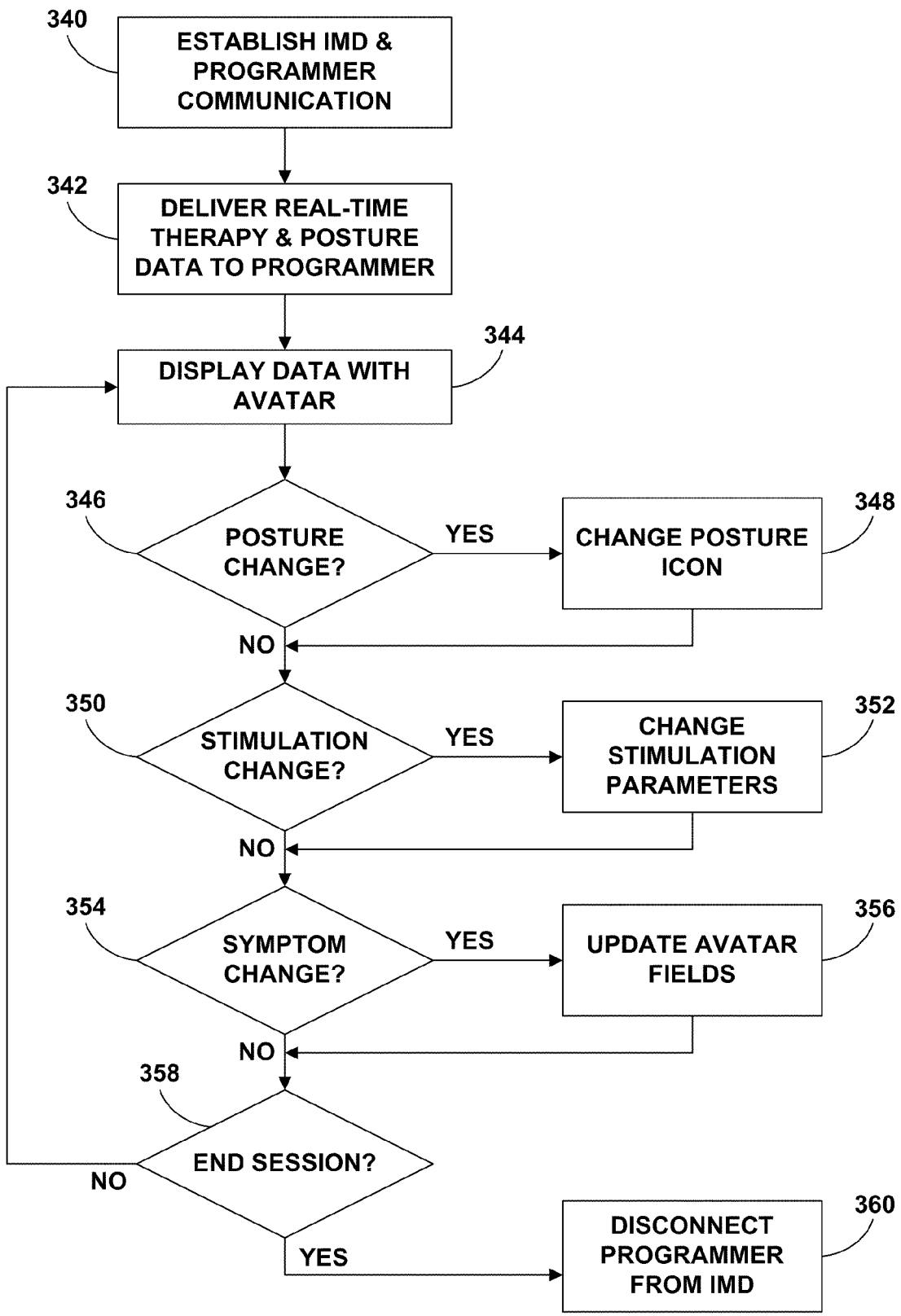
FIG. 16 is a flow diagram illustrating an example technique for displaying therapy information for a patient in real-time.

FIG. 16 is a flow chart illustrating an example technique for displaying therapy information for patient 12 in real-time. For purposes of illustration, user interface 200 of external programmer 20 and IMD 14 will be described. However, any combination of programmers 20, 30 and 60 could be used with IMD 14 or 26. As shown in FIG. 15, viewing therapy information begins by the clinician requesting that IMD 14 and external programmer 20 establish communication (340). Telemetry circuit 88 of IMD 14 then delivers real-time stimulation parameters, physiological conditions, and posture state data to telemetry circuit 110 of external programmer 20 (342).

User interface 200 displays the physiological conditions with avatar 204, the stimulation parameters in a stimulation field, and the posture state of patient 12 in a posture field (344). The stimulation parameters may be each provided or displayed as stimulation fields. If the posture state of patient 12 changes (346), user interface 200 changes the posture icon (348). In conjunction with the change of the posture icon indicating the posture state of patient 12, the physiological condition information and stimulation parameter information may also change to such information associated with the specific posture state of the patient indicated by the posture icon. If there is a change to any stimulation therapy (350), user interface 200 changes the stimulation parameters as they are presented to the user (352). If there are any specified changes to the conditions of patient 12 (354), user interface subsequently updates the fields of avatar 204 (356). In other examples the order of when user interface 200 and processor 104 determine these changes may be altered as needed.

If the user next decides to end the real-time programming session (358), external programmer 20 disconnects from IMD 14 (360). If the user has not specified that the session should end (358), then the programming session continues and user interface 200 continues to display the therapy information to the user. In addition, user interface 200 may perform other operations not explicitly described in FIG. 16.

A clinician, patient 12, or other user may utilize the example technique of FIG. 16 to program therapy parameter values and/or input physiological condition information associated with specific posture states of patient 12. For example, during a programming session, a clinician may instruct a patient 12 to occupy a posture state. When in that posture state, patient 12 may provide feedback regarding physiological conditions experienced, e.g., pain and/or paresthesia. The feedback from patient 12 may be communicated to user interface 200, and the physiological condition information may be associated with the posture state occupied by patient 12 and user interface 200 may be updated to reflect the patient feedback, e.g., on avatar 204 (FIG. 8). Additionally or alternatively, a clinician may program therapy parameter values for a patient posture state when the patient occupies the posture state. Adjustments or initials therapy parameter values indicated to user interface 200 may be associated with the posture state of patient 12 detected in real-time. In some examples, a clinician may be allowed to trial certain therapy parameter values for patient 12 when in the occupied posture state using user interface 200 to identify desirable and/or undesirable therapy parameter values for the posture state. As described above, adjustments made to physiological conditions, therapy parameters, and other therapy information may be communicated in real-time to IMD 14 from the external device, and/or may be communicated periodically, e.g., at the end of a programming session, to the IMD 14.

Figure 17:
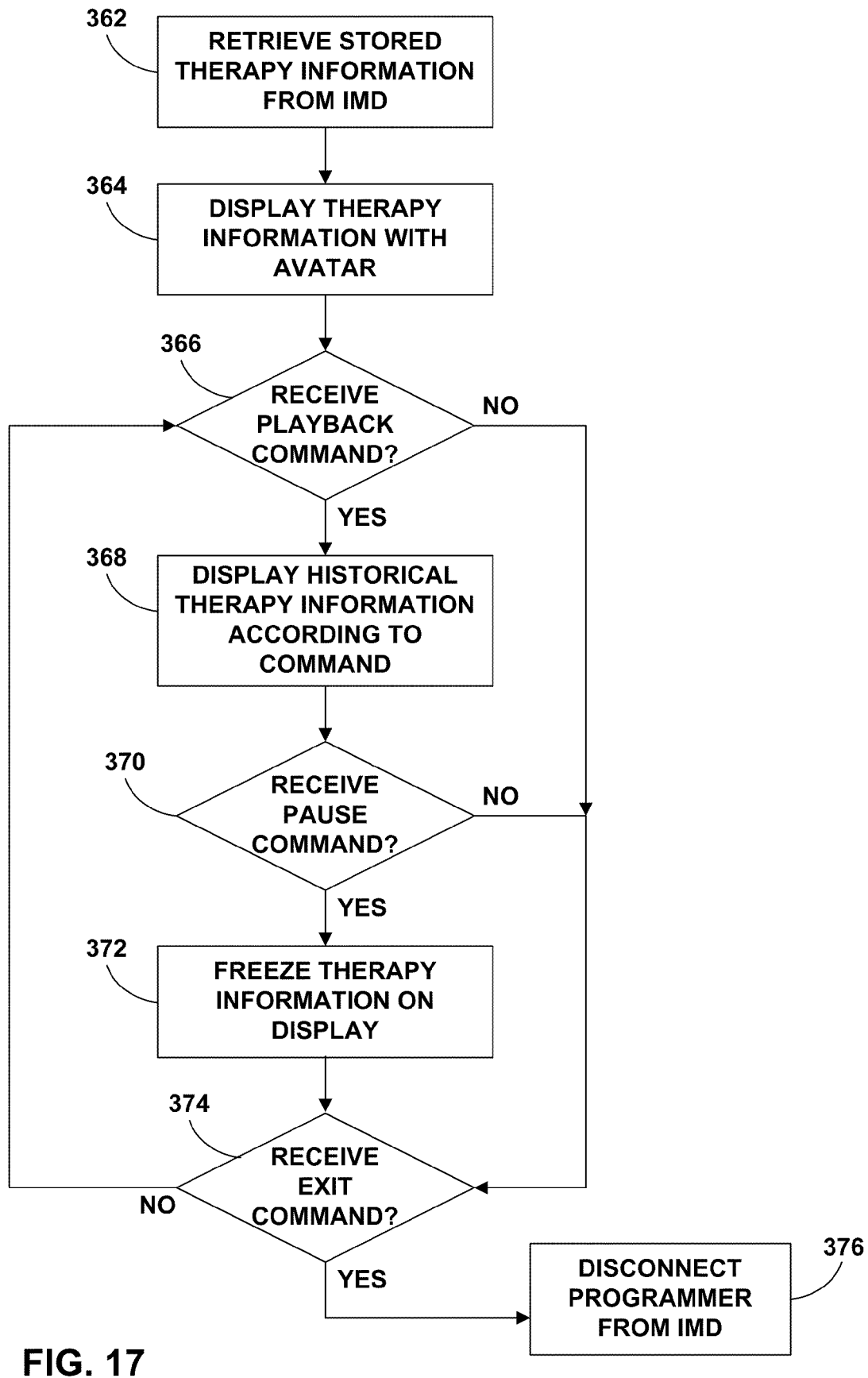
FIG. 17 is a flow diagram illustrating an example technique for displaying previously stored therapy information for a patient.

FIG. 17 is a flow chart illustrating an example technique for displaying previously stored therapy information of patient 12. For purposes of illustration, user interface 290 of external programmer 20 and IMD 14 will be described. However, any combination of programmers 20, 30 and 60 could be used with IMD 14 or 26. As shown in FIG. 17, telemetry circuit 110 of external programmer 20 retrieves stored therapy information from telemetry circuit 88 of IMD 14 (362). User interface 290 then displays the therapy information with conditions being overlaid on avatar 204 (364).

If user interface 290 receives a playback command (366), user interface 290 displays the new therapy information of the new identified time according to the playback command (368). If the playback command was to present a sequence or continual change, user interface 200 continues to change the therapy information presented according to the new identified time. If user interface 290 receives a selection of pause button 310 (370), then user interface 290 freezes the currently displayed therapy information on the display (372). If there is no command received to exit the screen of user interface 290 (374), user interface 290 does not change the displayed therapy information until another playback command is received (366).

If user interface 290 receives an exit command from the user (374), user interface 200 exits the screen of user interface 290 and external programmer 20 disconnects from IMD 14 (376). In some examples, no disconnection is necessary if no real-time communication was being used. For example, the default mode of communication between IMD 14 and external programmer 20 may be for IMD 14 to only transmit data when requested by external programmer 20. This type of data transfer may conserve the battery power of IMD 14.

The disclosure may be capable of providing many features to a user. For example, real-time posture state data can be provided along with stimulation parameters and condition information on the same user interface. This may help a clinician to create an intuitive and less complicated tool for patient and clinician programming. The posture state data can also be used to ensure that the posture state of the patient is accurately detected by the IMD, leading to fewer mistakes during posture related programming. In addition, the playback of historical therapy information may facilitate troubleshooting for difficult to treat symptoms.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

If implemented in software, the techniques described in this disclosure may be stored on or transmitted over as one or more instructions or code on a computer-readable medium. Computer-readable media may include non-transitory computer storage media or communication media including any medium that facilitates transfer of a computer program from one place to another. Data storage media may be any available media that can be accessed by one or more computers or one or more processors to retrieve instructions, code and/or data structures for implementation of the techniques described in this disclosure. By way of example, and not limitation, such data storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The code may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

In addition, it should be noted that the systems described herein may not be limited to treatment of a human patient. In alternative embodiments, these systems may be implemented in non-human patients, e.g., primates, canines, equines, pigs, and felines. These animals may undergo clinical or research therapies that may benefit from the subject matter of this disclosure.

Many embodiments of the disclosure have been described. Various modifications may be made without departing from the scope of the claims. These and other embodiments are within the scope of the following claims.

The invention claimed is:

1. A method comprising:
displaying, via a user interface of a programmer device configured to program a medical device, a posture state field representative of a posture state of a patient;
displaying, via the user interface, at least one graphical representation representative of at least a portion of a body of the patient;
displaying, via the user interface, a physiological condition indicator on at least a portion of the portion of a body of the patient represented by the graphical representation, wherein the physiological condition indicator is indicative of a physiological condition of the patient associated with the posture state of the patient;
displaying, via the user interface, at least one of a plurality of therapy parameters that define therapy delivered to the patient from the medical device when the patient occupies the posture state represented by the displayed posture state field, wherein the therapy defined by the plurality of therapy parameters comprises at least one of electrical stimulation therapy or therapeutic agent delivery therapy;
receiving user input indicating an adjustment to the at least one of the plurality of therapy parameters displayed on the user interface;
transmitting, from the programmer device to the medical device, information defining the at least one of the plurality of therapy parameters based on the adjustment indicated by the received user input; and
controlling the delivery of the therapy to the patient via the medical device based at least in part on the transmitted information, and wherein delivery of the at least one of electrical stimulation therapy or therapeutic agent delivery therapy to the patient is controlled according to a determined posture state of the patient.

2. The method of claim 1, wherein the at least one of the plurality of therapy parameters displayed are associated with the posture state of the patient.

3. The method of claim 1, wherein the posture state field changes in real-time according to posture state data received from the medical device, and wherein the medical device is configured to detect the posture state occupied by the patient.

4. The method of claim 1, wherein the posture state field comprises a posture icon that graphically represents the posture state of the patient.

5. The method of claim 1, further comprising displaying a therapy adjustment field configured to receive the user input indicative of the adjustment to at least one of a plurality of therapy parameters that defines the therapy for the posture state represented by the posture state field.

6. The method of claim 1, wherein displaying at least one of a plurality of therapy parameters comprises displaying a therapy field icon in relation to a target anatomy that graphically represents the at least one therapy parameter.

7. The method of claim 6, further comprising displaying the at least one therapy parameter represented by the therapy icon in a pop-up window.

8. The method of claim 1, further comprising displaying a playback field configured to accept a playback command that enables a user to review previously stored therapy information on a temporal basis.

9. The method of claim 1, further comprising receiving therapy information from the medical device, wherein the therapy information comprises at least one of posture state information, physiological condition information, and therapy parameter information.

10. The method of claim 1, wherein the therapy delivered to the patient comprises electrical stimulation therapy.

11. A system comprising:
a programmer device configured to program a medical device, the programmer device including a user interface display; and
a processor configured to control the user interface display;
wherein, under control of the processor, the user interface is configured to display a posture state field representative of a posture state of a patient, display at least one graphical representation representative of at least a portion of a body of the patient, display a physiological condition indicator on at least a portion of the portion of a body of the patient represented by the graphical representation, and display at least one of a plurality of therapy parameters that define therapy delivered to the patient,
wherein the physiological condition indicator is indicative of a physiological condition of the patient associated with the posture state of the patient from the medical device when the patient occupies the posture state represented by the displayed posture state field, wherein the therapy defined by the plurality of therapy parameters comprises at least one of electrical stimulation therapy or therapeutic agent delivery therapy, wherein the processor is configured to receive user input indicating an adjustment to the at least one of the plurality of therapy parameters displayed on the user interface, transmit, from the programmer device to the medical device, information defining at least one of the plurality of therapy parameters based on the adjustment indicated by the received user input, and control the delivery of the therapy to the patient via the medical device based at least in part on the transmitted information, and wherein delivery of the at least one of electrical stimulation therapy or therapeutic agent delivery therapy to the patient is controlled according to a determined posture state of the patient.

12. The system of claim 11, further comprising the medical device including a posture state module configured to detect the posture state of the patient, and a first telemetry circuit configured to transmit the detected posture state to the programmer device.

13. The system of claim 12, wherein the first telemetry circuit transmits the detected posture state to the programmer device in real-time, and the user interface updates the posture state field in real-time according to the detected posture state.

14. The system of claim 11, wherein the at least one of the plurality of therapy parameters displayed by the user interface are associated with the posture state of the patient.

15. The system of claim 11, wherein the posture state field comprises a posture icon that graphically represents the posture state of the patient.

16. The system of claim 11, wherein the user interface displays a therapy adjustment field configured to receive the user input indicative of the adjustment to at least one of a plurality of therapy parameters defining the therapy for the posture state represented by the posture state field.

17. The system of claim 16,
wherein the medical device comprises a processor, a memory, and a first telemetry circuit,
wherein the programmer device comprises a second telemetry circuit,
wherein the second telemetry circuit transmits the received adjustment to the at least one stimulation parameter and the first telemetry circuit receives the received adjustment to the at least one therapy parameter, and
wherein the processor stores the received adjustment to the at least one therapy parameter in the memory for subsequent therapy delivery to the patient.

18. The system of claim 11, wherein the user interface displays the at least one therapy parameter by displaying a therapy icon in relation to a target anatomy that graphically represents the at least one therapy parameter.

19. The system of claim 11, wherein the programmer device comprises a memory configured to store therapy information received from the medical device, the therapy information comprising at least one of postures state information, physiological condition information, and therapy parameter information.

20. The system of claim 19, wherein the user interface displays a playback field configured to accept a playback command enabling a user to review the therapy information stored in the memory on a temporal basis.

21. The system of claim 11, wherein the processor comprises a first processor and a second processor, the system further comprising the medical device including a therapy module and the second processor,
wherein the second processor is configured to control the therapy module to deliver the therapy to the patient, and
wherein the therapy comprises electrical stimulation therapy.

22. A non-transitory computer-readable storage medium comprising instructions that cause a processor to control a user interface of a programmer device configured to program a medical device to:
display a posture state field representative of a posture state of a patient;
display at least one graphical representation representative of at least a portion of a body of the patient;
display a physiological condition indicator on at least a portion of the portion of a body of the patient represented by the at least one graphical representation, wherein the condition indicator is indicative of a physiological condition of the patient associated with the posture state of the patient;
display at least one of a plurality of therapy parameters that define therapy delivered to the patient from the medical device when the patient occupies the posture state represented by the displayed posture state field, wherein the therapy defined by the plurality of therapy parameters comprises at least one of electrical stimulation therapy or therapeutic agent delivery therapy, receive user input indicating an adjustment to the at least one of the plurality of therapy parameters displayed on the user interface;

cause the processor to control a telemetry interface to transmit, from the programmer device to the medical device, information defining the at least one of the plurality of therapy parameters based on the adjustment indicated by the received user input; and control the delivery of the therapy to the patient via the medical device based at least in part on the transmitted information, and wherein delivery of the at least one of electrical stimulation therapy or therapeutic agent delivery therapy to the patient is controlled according to a determined posture state of the patient.

23. A system comprising:

means for displaying, via a user interface of a programmer device configured to program a medical device, a posture state field representative of a posture state of a patient, displaying at least one graphical representation representative of at least a portion of a body of the patient, displaying at least one of a plurality of therapy parameters that define therapy delivered to the patient from the medical device when the patient occupies the posture state represented by the displayed posture state field, and displaying a physiological condition indicator on at least a portion of the portion of a body of the patient represented by the graphical representation, wherein the physiological condition indicator is indicative of a physiological condition of the patient associated with the posture state of the patient, wherein the therapy defined by the plurality of therapy parameters comprises at least one of electrical stimulation therapy or therapeutic agent delivery therapy;

means for determining the posture state field, the at least one graphical representation, and the physical condition indicator;

means for receiving user input indicating an adjustment to the at least one of the plurality of therapy parameters displayed on the user interface;

means for transmitting, from the programmer device to the medical device, information defining the at least one of the plurality of therapy parameters based on the adjustment indicated by the received user input; and means for controlling the delivery of the therapy to the patient via the medical device based at least in part on the transmitted information, and wherein delivery of the at least one of electrical stimulation therapy or therapeutic agent delivery therapy to the patient is controlled according to a determined posture state of the patient.

* * * * *